United States Patent
Lin

(10) Patent No.: US 12,281,133 B2
(45) Date of Patent: *Apr. 22, 2025

(54) HYALURONAN CONJUGATE

(71) Applicant: Aihol Corporation, Buena Park, CA (US)

(72) Inventor: Hua-Yang Lin, Taipei (TW)

(73) Assignee: Aihol Corporation, Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/123,645

(22) Filed: Mar. 20, 2023

(65) Prior Publication Data

US 2023/0227490 A1 Jul. 20, 2023

Related U.S. Application Data

(62) Division of application No. 17/341,694, filed on Jun. 8, 2021, now Pat. No. 11,643,431.

(60) Provisional application No. 63/130,442, filed on Dec. 24, 2020, provisional application No. 63/036,231, filed on Jun. 8, 2020.

(51) Int. Cl.
| | |
|---|---|
| *C07H 19/056* | (2006.01) |
| *A61K 31/7016* | (2006.01) |
| *A61K 31/728* | (2006.01) |
| *A61P 11/00* | (2006.01) |

(52) U.S. Cl.
CPC ....... *C07H 19/056* (2013.01); *A61K 31/7016* (2013.01); *A61K 31/728* (2013.01); *A61P 11/00* (2018.01)

(58) Field of Classification Search
None
See application file for complete search history.

(56) References Cited

U.S. PATENT DOCUMENTS

| | | | | |
|---|---|---|---|---|
| 11,643,431 B2* | 5/2023 | Lin | | A61K 31/7016 |
| | | | | 514/43 |
| 2017/0015336 A1* | 1/2017 | Bartek | | H04B 1/69 |
| 2017/0151336 A1* | 6/2017 | Lin | | A61K 31/145 |

FOREIGN PATENT DOCUMENTS

| | | |
|---|---|---|
| JP | 2016-529362 A | 9/2016 |
| TW | 201509422 B | 3/2015 |

OTHER PUBLICATIONS

Journal Jian, Y S, et al. Hyaluronic acid—nimesulide conjugates as anticancer drugs against CD44-overexpressing HT-29 colorectal cancer in vitro and in vivo Int J Nanomedicine vol. 12 Int J Nanomedicine 2017 pp. 2315-2333. Mar. 27, 2017.
Kang et al, "Targeting Interleukin-6 signalling in clinic", Immunity, 50, pp. 1007-1023, Apr. 16, 2019 (Apr. 16, 2019).
Jingping Sun, Gabriela P. Law, Christy C. Bridges, Robert J. McKallip, CD44 as a novel target for treatment of staphylococcal enterotoxin B-induced acute inflammatory lung injury, Clinical Immunology, 2012, vol. 144, pp. 41-52.
Zhenyu Yang et al, Protective effect of nimesulide on acute lung injury in mice with severe acute pancreatitis, Am J Transl Res, 2019, vol. 11(9), pp. 6024-6031.

* cited by examiner

*Primary Examiner* — Traviss C McIntosh, III
(74) *Attorney, Agent, or Firm* — patenttm.us

(57) ABSTRACT

Disclosed herein are hyaluronic acid (HA)-nimesulide conjugates having one or two disaccharide units.

4 Claims, 16 Drawing Sheets

Mean±SD

: p< 0.05 vs negative control   *: p < 0.05 vs positive control

Mean±SD

: p< 0.05 vs negative control    *: p < 0.05 vs positive control

HYALURONAN CONJUGATE

CROSS-REFERENCE TO RELATED APPLICATIONS

This application is a divisional applications of U.S. non-provisional application Ser. No. 17/341,694, filed on Jun. 8, 2021, which claims the benefits of U.S. Provisional Application No. 63/036,231, filed on Jun. 8, 2020, and No. 63/130,442, filed on Dec. 24, 2020, which are hereby incorporated herein by reference in entirety.

BACKGROUND OF THE INVENTION

1. Field of the Invention

The present disclosure relates to hyaluronic conjugates; more particularly, to hyaluronic conjugates for treating pulmonary inflammation.

2. Description of Related Art

Inflammation is a process by which our body's immune system response to stimuli, such as pathogens, irritants, and injury, among others. There are two types of inflammation: acute inflammation and chronic inflammation. Key signs of acute inflammation include pain, redness, swelling, and heat, which often last a few days. On the other hand, chronic inflammation can take place for months or even years. The common symptoms for chronic inflammation include pain and fatigue; in contrast, the other symptoms often depend on the diseases associated with the chronic inflammation, such as allergies, arthritis, psoriasis, rheumatoid arthritis, diabetes, cardiovascular diseases, and chronic obstructive pulmonary disease (COPD).

The inflammatory response is the result of a very complex cascade of events originating at the site of stimuli. This complex response is mediated by cytokines. Cytokines are key modulators of inflammation, participating in adaptive immunity, pro-inflammatory signaling pathway, and anti-inflammatory signaling pathway. Examples of cytokines include, but are not limited to, chemokines, interleukins (ILs), tumor necrosis factors (TNFs, e.g., TNF-α and TNF-β, interferons (IFNs, e.g., IFN-α, IFN-β, and IFN-γ), colony stimulating factors (CFS, e.g., granulocyte CSF (G-CSF) and granulocyte/macrophage CSF (GM-CSF), macrophage CSF (M-CSF), and erythropoietin), and transforming growth factor beta (TGF-β). Chemokines are a family of small cytokines (8-12 kDa), which are produced by cells primarily to recruit leukocytes to the sites of stimuli. Chemokines can be categorized into four groups depending on the spacing of their first two N-terminal cysteine residues: CC chemokines, C chemokines, CXC chemokines, and CX3C chemokines.

IL-6 is a versatile cytokine, participating in host defense against acute environmental stimuli, such as infections and tissue injuries, by activating acute-phase reactions, immune responses, and hematopoiesis. However, the dysregulated continuous production of IL-6 may cause the onset and development of various autoimmune and chronic inflammatory diseases. Further, high expression of IL-6 and some other cytokines (such as IFN-γ and IL-10) may lead to cytokine release syndrome (CRS), or cytokine storm, a systemic acute inflammatory complication. The current pandemic of COVID-19 has put pressure on the medical resources and socioeconomics of many countries. COVID-19 is an infectious disease caused by severe acute respiratory syndrome coronavirus 2 (SARS-CoV-2). In severe COVID-19 patients, CRS of varying degrees are seen, and these patients often have an elevated level of IL-6. Since CRS can trigger severe lung damage and potentially lead to acute respiratory distress syndrome (ARDS) and death, blocking the IL-6-mediated cascade may reduce disease severity.

Therefore, IL-6 blockade has been a treatment strategy for autoimmune, inflammatory diseases, and cytokine storm. However, since the immune response is quite complicated and dynamic, only a few IL-6 blockade drugs have been approved, with several drug candidates in clinical trials. Nonetheless, all these drugs are antibody-based biologics, which are often very expensive, especially in their early years of launch.

In view of the foregoing, there exists a need in the art for providing a small-molecule-based therapeutic agent that can effectively

SUMMARY

The following presents a simplified summary of the disclosure in order to provide a basic understanding to the reader. This summary is not an extensive overview of the disclosure, and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a method for treating pulmonary inflammation in a subject in need thereof.

According to some embodiments of the present disclosure, the method comprises the step of administering to the subject an effective amount of a hyaluronan conjugate having at least one disaccharide unit having the structure of,

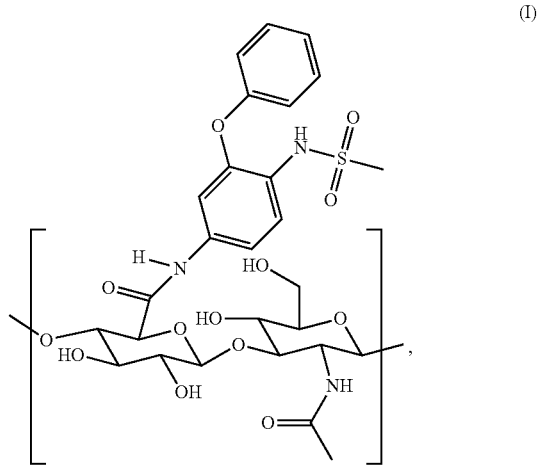

(I)

or pharmaceutically acceptable salt thereof.

In various embodiments, the subject is a mammal, including humans.

According to some embodiments of the present disclosure, the pulmonary inflammation is acute pulmonary inflammation (e.g., pneumonia, acute respiratory distress syndrome (ARDS), and acute lung injury (ALI)), chronic pulmonary inflammation (e.g., chronic obstructive pulmonary disease (COPD), asthma, pulmonary fibrosis, or idiopathic pulmonary fibrosis (IPF)), or hypersensitivity pneumonitis (extrinsic allergic alveolitis).

According to various embodiments of the present disclosure, pneumonia is caused by bacteria (e.g., Staphylococcus aureus, Pseudomonas aeruginosa, Streptococcus pneumoniae, Klebsiella pneumoniae, and Mycobacteria), viruses (e.g., influenza viruses, respiratory syncytial viruses (RSV), adenoviruses, herpes simplex viruses (HSV), and coronaviruses), or parasites (e.g., Leishmania, Plasmodium, and Schistosoma). Examples of coronaviruses capable of causing pneumonia in human include, but are not limited to severe acute respiratory syndrome-related coronavirus (SARS-CoV), severe acute respiratory syndrome-related coronavirus 2 (SARS-CoV-2), and Middle East respiratory syndrome-related coronavirus (MERS-CoV).

In some embodiments, the hyaluronan conjugate is administered via intravenous (i.v.) injection.

According to certain embodiments of the present disclosure, the hyaluronan conjugate has an average molecular weight (MW) of 10 to 2,000 kilodaltons (kDa); preferably, 50 to 250 kDa; more preferably, 100 to 200 kDa.

According to some embodiments of the present disclosure, the hyaluronan conjugate has a degree of substitution (DS) of about 0.5% to 35%; that is, for every 1,000 disaccharide units, there are about 5 to 100 hydrogenated nimesulide molecules conjugated thereto. In some preferred embodiments, the DS of the present hyaluronan conjugate is about 0.75 to 9%; preferably, about 1% to 8%; preferably, about 1.25% to 7%; preferably, 1.5% to 6%; preferably, about 1.75% to 5.5%; preferably, about 2% to 5%; preferably, about 2.25% to 4.5%.

According to certain embodiments of the present disclosure, the hyaluronan conjugate comprises only one disaccharide unit and has the structure of,

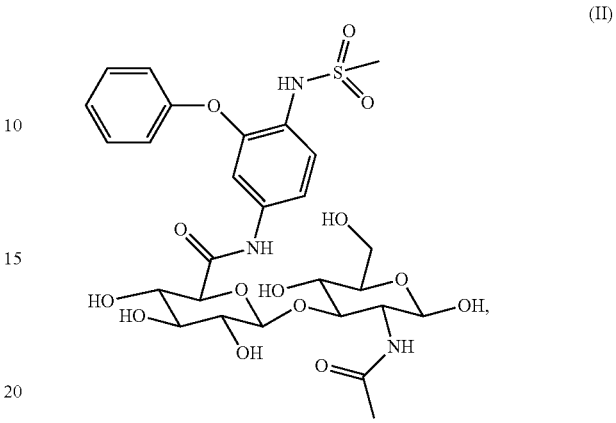

(II)

or pharmaceutically acceptable salt thereof.

According to certain embodiments of the present disclosure, the hyaluronan conjugate comprises only two disaccharide units and has the structure of,

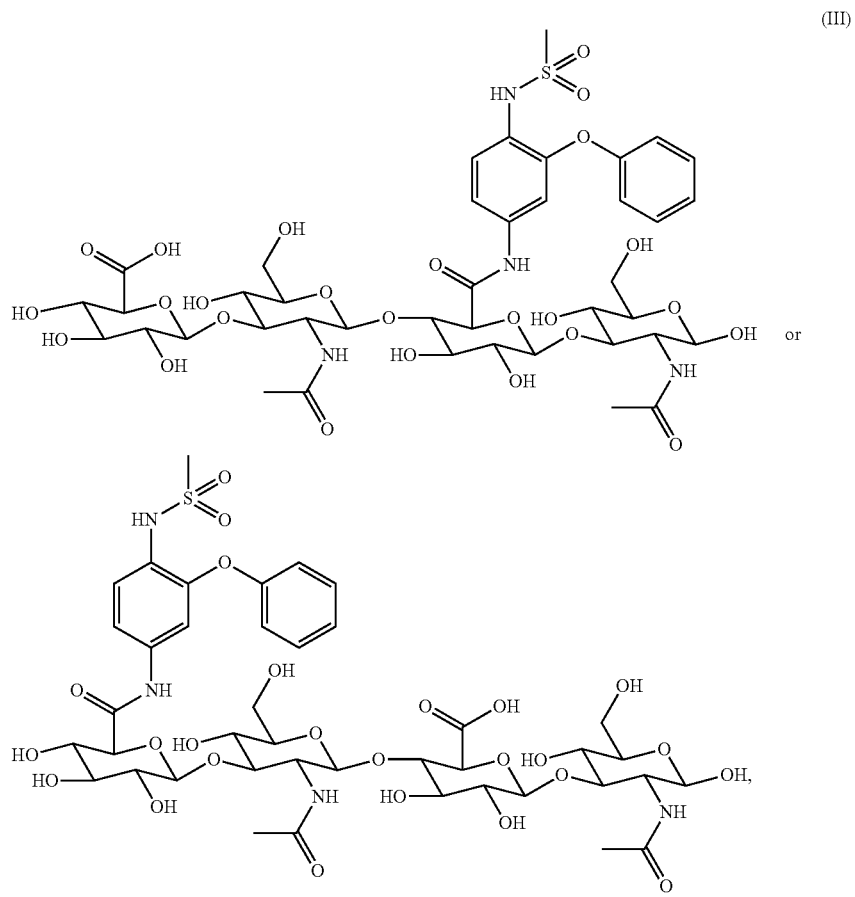

(III)

or pharmaceutically acceptable salt thereof.

In still another aspect, the present disclosure is directed to a pharmaceutical composition for treating pulmonary inflammation.

According to some embodiments, the pharmaceutical composition comprises an effective amount of a hyaluronic conjugate as described above and a pharmaceutically-acceptable excipient.

Subject matters that are also included in other aspects of the present disclosure include the use of a hyaluronic conjugate in the manufacture of a medicament for use in the treatment of pulmonary inflammation, as well as a hyaluronic conjugate for use in the treatment of pulmonary inflammation.

Many of the present disclosure's attendant features and advantages will become better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1:
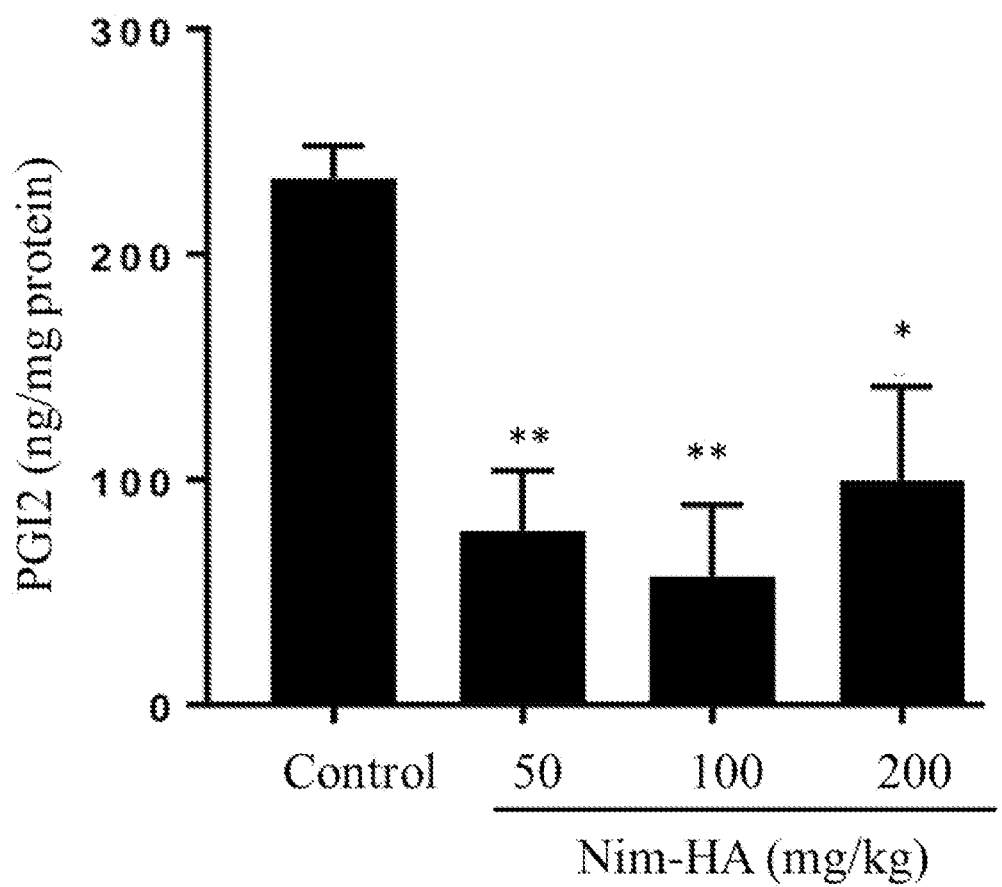
FIG. 1 is a histogram illustrating the PGI2 level in mice in different experimental groups according to one working example of the present disclosure.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples, and appended claims are collected here. Unless otherwise defined herein, scientific and technical terminologies employed in the present disclosure shall have meanings commonly understood and used by one of ordinary skill in the art.

Unless otherwise required by context, it will be understood that singular terms shall include plural forms of the same, and plural terms shall include the singular. Also, as used herein and in the claims, the terms "at least one" and "one or more" have the same meaning and include one, two, three, or more. Furthermore, the phrases "at least one of A, B, and C," "at least one of A, B, or C," and "at least one of A, B and/or C" as used throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. However, any numerical value inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints unless specified otherwise.

The terms "treatment" and "treating" as used herein may refer to a preventative (e.g., prophylactic), curative or palliative measure. In particular, the term "treating" as used herein refers to the application or administration of the present hyaluronan conjugate or a pharmaceutical composition comprising the same to a subject, who has a medical condition, a symptom associated with the medical condition, a disease or disorder secondary to the medical condition, or a predisposition toward the medical condition, with the purpose to partially or wholly alleviate, ameliorate, relieve, delay the onset of, inhibit the progression of, reduce the severity of, and/or reduce the incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The terms "subject" and "patient" are used interchangeably herein and are intended to mean an animal including the human species that is treatable by the hyaluronan conjugate described herein, pharmaceutical compositions comprising the same, and/or methods of the present invention. Accordingly, the term "subject" or "patient" comprises any mammal, which may benefit from the present disclosure. The term "mammal" refers to all members of the class Mammalia, including humans, primates, domestic and farm animals, such as rabbit, pig, sheep, and cattle; as well as zoo, sports, or pet animals; and rodents, such as mouse and rat. The term "non-human mammal" refers to all members of the class Mammalis except humans. In one exemplary embodiment, the patient is a human. The term "subject" or "patient" are intended to refer to both the male and female gender unless one gender is specifically indicated.

The terms "application" and "administration" are used interchangeably herein to mean the application of a hyaluronan conjugate or a pharmaceutical composition of the present invention to a subject in need of a treatment thereof.

The term "effective amount," as used herein, refers to the quantity of the present hyaluronan conjugate that is sufficient to yield a desired therapeutic response. An effective amount of an agent is not required to cure a disease or condition but will provide treatment for a disease or condition such that the onset of the disease or condition is delayed, hindered, or prevented, or the disease or condition symptoms are ameliorated. The effective amount may be divided into one, two, or more doses in a suitable form to be administered at one, two, or more times throughout a designated period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. The effective amount may be expressed, for example, as the total mass of the hyaluronan conjugate or the equivalent mass of the 4-aminonimesulide in the hyaluronan conjugate (e.g., in grams, milligrams, or micrograms) or a ratio of the mass of the hyaluronan conjugate or the equivalent mass of the 4-aminonimesulide in the hyaluronan conjugate to body mass, e.g., as milligrams per kilogram (mg/kg).

For example, according to some working examples of the present disclosure, the effective amount of the hyaluronan conjugate for treating the inflammation in mice (about 20 grams) by lowering their IL-6, KC-GRO, and MCP-1 levels is about 25 to 150 mg/kg body weight/dose. Therefore, the effective amount of the hyaluronan conjugate for treating mice is about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 mg/kg body weight/dose. In an adult human weighting approximately 60 kg, the human equivalent dose (HED) derived from the above-described doses for mice is about 2 to 120 mg/kg body weight/dose.

As could be appreciated, the dosage ranges described above are provided as guidance for the administration of provided pharmaceutical compositions to an adult. The amount to be administered to, for example, a child or an adolescent can be determined by a medical practitioner or person skilled in the art and can be lower, or the same as that administered to an adult. Considering the age, weight, and health condition of the patient, the effective amount for a human subject can be about 1 to 200 mg/kg body weight/dose.

Specifically, the effective amount of the hyaluronan conjugate for a human subject may be 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 mg/kg body weight/dose.

Also, the effective amount for treating mice (about 20 grams) in terms of the equivalent mass of the 4-aminonimesulide in the hyaluronan conjugate is about 50 ng/kg body weight to 6 µg/kg; for example, about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 ng/kg body weight/dose, or 1, 1.5, 2, 2.5, 3, 3.5, 4, 4.5, 5, 5.5, or 6 µg/kg body weight/dose.

Similarly, in an adult human weighing approximately 60 kg, the HED of the equivalent mass of the 4-aminonimesulide in the hyaluronan conjugate derived from the above-described doses for mice (conversion factor: 0.08) is about 4 to 480 ng/kg body weight/dose. In sum, the HED for the present hyaluronan conjugate is about 80 ng/kg body weight to 400 µg/kg body weight/dose. Considering the age, weight, and health condition of the patient, the effective amount for a human subject can be about 20 to 840 ng/kg body weight/dose.

Specifically, the effective amount for a human subject may be 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, or 840 ng/kg body weight/dose.

According to examples of the present disclosure, the hyaluronan conjugate is administered three times weekly for two weeks. As could be appreciated, the effective amount can be adjusted accordingly depending on the interval and duration of administration. In certain embodiments, when multiple doses are administered to a subject, the frequency of administering the multiple doses to the subject is three doses a day, two doses a day, one dose a day, one dose every other day, one dose every third day, one dose every fourth day, one dose every fifth day, one dose every sixth day, one dose every week, one dose every other week, one dose monthly or one dose every other month. In certain embodiments, the frequency of administering the multiple doses to the subject is one dose per day. In certain embodiments, the frequency of administering the multiple doses to the subject is two doses per day. In certain embodiments, when multiple doses are administered to a subject, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject. In certain embodiments, the duration between the first and last doses of the multiple doses is three months, six months, or one year. In certain embodiments, the duration between the first and last doses of the multiple doses is the subject's lifetime. In a specific embodiment, the frequency of administering the multiple doses to the subject is three doses per week.

Also, according to the examples provided hereinbelow, the hyaluronan conjugate is administered via i.v. injection; however, this is only an illustration as to how the present invention can be implemented, and the present disclosure is not limited thereto.

For example, the hyaluronan conjugate can be formulated, together with a pharmaceutically-acceptable excipient, into a pharmaceutical composition suitable for the desired administration mode. Certain pharmaceutical compositions prepared in accordance with the presently disclosed and claimed inventive concept(s) are single unit dosage forms suitable for oral, mucosal (e.g., nasal, sublingual, vaginal, buccal, or rectal), parenteral (e.g., subcutaneous, intravenous, bolus injection, intramuscular, or intraarterial), intravitreal, or transdermal administration to a patient. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. As could be appreciated, these pharmaceutical compositions are also within the scope of the present disclosure.

The phrase "pharmaceutically acceptable excipient" as used herein means a pharmaceutically acceptable material, composition or vehicle, such as a liquid or solid filler, diluent, carrier, solvent or encapsulating material, involved in carrying or transporting the subject agents from one organ, or portion of the body, to another organ, or portion of the body. Each excipient must be "acceptable" in the sense of being compatible with the other ingredients of the formulation. The pharmaceutical formulation contains a compound of the invention in combination with one or more pharmaceutically acceptable ingredients. The excipient can be in the form of a solid, semi-solid or liquid diluent, cream, or a capsule. These pharmaceutical preparations are a further object of the invention. Usually, the amount of active compounds is between 0.1-95% by weight of the preparation, preferably between 0.2-20% by weight in preparations for parenteral use, and preferably between 1 and 50% by weight in preparations for oral administration. For the clinical use of the methods of the present invention, the pharmaceutical composition of the invention is formulated into formulations suitable for the intended route of administration.

The term "degree of substitution (DS)" of the HA conjugate, as used herein, is the average ratio of substituent groups (i.e., the hydrogenated nimesulide) attached per disaccharide unit of the HA. According to various embodiments of the present disclosure, the hyaluronan conjugate has a degree of substitution of 0.5% to 35%. For example, the degree of substitution may be 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30 or 35%.

According to certain embodiments of the present disclosure, the hyaluronan conjugate has an average molecular weight (MW) of 10 to 300 kilodaltons (kDa). For example, the MW may be 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000 kDa. The average molecular is obtained using a viscometer, and according to various embodiment of the present disclosure, the viscosity of the hyaluronan conjugate is about 0.1 to 1 $m^3$/kg; for example, 0.1, 0.2, 0.3, 0.4, 0.5, 0.6, 0.7, 0.8, 0.9, or 1 $m^3$/kg. According to some embodiments of the present disclosure, the hyaluronan conjugate comprises two saccharide units (i.e., one hyaluronan monomer) or four saccharide units (i.e., two hyaluronan monomers).

As used herein, the term "hyaluronic acid" (HA) (also called hyaluronate or hyaluronan) is an anionic, nonsulfated glycosaminoglycan composed of at least one disaccharide unit, specifically a D-glucuronic acid and an N-acetyl-D-glucosamine (-4GlcUAβ1-3GlcNAcβ1-). In some embodiments of the present disclosure, the HA consists of a single disaccharide unit (i.e., HA disaccharide). In some embodiments of the present disclosure, the HA consists of two disaccharide units (i.e., HA tetrasaccharide). The molecular weight of HA can range from 379 Dalton (Da) (a single disaccharide unit) to millions of daltons. HA is involved in cell motility and immune cell adhesion by interaction with the cell surface receptor for hyaluronan-mediated motility (RHAMM) and CD44. The term "HA derivative" refers to an HA having any modification on the hydroxyl, carboxyl, amide, or acetylamino groups of one or more disaccharide units of the HA. According to certain embodiments of the present disclosure, the HA conjugates are in the form of a metal salt, preferably an alkali metal salt, and more preferably a sodium or potassium salt.

The present disclosure is based, at least in part, on the discovery that, in IL-6 overexpression mice, the hyaluronan conjugate can lower the expression level of IL-6, as well as the expression of downstream mediator CCL2 (or monocyte chemoattractant protein-1 (MCP-1) and CXCL1/2 (or keratinocyte chemoattractant (KC) chemokine, mouse homologues of human growth-regulated oncogenes (GRO)). Accordingly, the present hyaluronan conjugate can be used to block the signaling cascade downstream of IL-6. Since the IL-6 blockade has been shown to be beneficial both in experimental animal models and in human disease related to inflammation, the inhibition of IL-6 signaling with the present hyaluronan conjugate could prevent or reverse some of the complications typically associated with inflammation.

The present disclosure is further based on the discovery that the present hyaluronan conjugate can be used to inhibit the coronavirus (e.g., SARS-CoV-2) infection, at least by blocking the viral entry. According to various embodiments of the present disclosure, the present hyaluronan conjugate may work in dual modalities for treating SARS-CoV-2 virus infection (including coronavirus disease 2019 (COVID-19)) by (1) blocking the IL-6 dependent signaling cascade and (2) blocking the viral entry.

In view of the foregoing, the present disclosure proposes methods for treating inflammation, particularly pulmonary inflammation using the hyaluronan conjugate presented herein. Some embodiments of the present disclosure are directed to methods for treating symptoms or conditions associated with or secondary to pulmonary inflammation using said hyaluronan conjugate. Also provided herein is the use of said hyaluronan conjugate in the treatment of pulmonary inflammation, as well as its use in the manufacture of a medicament for said treatment purpose. The medicament (i.e., a pharmaceutical composition comprising the hyaluronan conjugate) is, of course, a subject matter covered by the scope of the present application.

The following Examples are provided to elucidate certain aspects of the present invention and aid those skilled in the art in practicing this invention. These Examples are in no way to be considered to limit the scope of the invention in any manner. Without further elaboration, it is believed that one skilled in the art can, based on the description herein, utilize the present invention to its fullest extent.

EXAMPLE 1

Synthesis and Characterization of NIM-HA Conjugate
(1) Preparation of Hydrogenated Nimesulide (H-NIM)

Hydrogenated nimesulide (N-(4-amino-2-phenoxyphenyl)methanesulfonamide, or 4-aminonimesulide) was synthesized from commercially purchased nimesulide (N-(4-nitro-2-phenoxyphenyl)methanesulfonamide). Briefly, 500 mg of nimesulide was completely dissolved in 20 ml ethyl acetate, and then 200 mg of 5% Pd/C (palladium on carbon) as catalyst was added into the solution. The air was extracted from the bottle under continued stir, and the air was replaced by hydrogen gas of up to 1 atm., followed by stirring for 24 hours to obtain the hydrogenated nimesulide (H-NIM).

The purity of the H-NIM was determined using thin-layer chromatography (TLC) on pre-coated TLC plates with silica gel 60 F254 under 254 nm UV light; mobile phase: hexane:ethyl acetate=2:1.

The Pd/C catalyst was removed by filtration, and the filtrate was concentrated on a rotary evaporator to remove the residual solvent. The hydrogenated product was then dissolved in hexane-ethyl acetate (1:1) solution for further purification on a silica gel column. The column was eluted with the elution solution (hexane-ethyl acetate=1:1). The fraction with color was collected and freeze-dried. The concentration and the structure of the resultant product were confirmed using UV and NMR, respectively.

(2) Conjugation of H-NIM and HA 50 mg of hyaluronic acid (with an average molecular weight (MW) of about 90-200 kDa) was dissolved in 25 ml d.d. water. 25.1 mg of 1-ethyl-3-(dimethylaminopropyl) carbodiimide hydrochloride (EDC) and 15.1 mg of N-hydroxyl succinimide (NHS) were mixed in 1 ml d.d. water and stirred at room temperature for 5 minutes. 3.65 mg of H-NIM mg was dissolved in 1 ml dimethyl sulfoxide (DMSO) solution, and then the solution was slowly dropped into HA/EDC/NHS solution using a syringe within 3 minutes. The reaction mixture was stirred at room temperature for 12 hours in the dark and then dialyzed for 2-3 days against an excess of d.d. water using a dialyzer bag (MWCO: 3,500 Da). The retentate was then freeze-dried to obtain NIM-HA (CA102N) powder.

(3) Characterization of NIM-HA Conjugate

The intrinsic viscosity (about 0.2 to 0.6 $m^3/kg$) of the conjugate was measured according to the procedure defined in the European Pharmacopoeia (HA monograph N° 1472), and the MW of the conjugated, as calculated from the intrinsic viscosity, was about 53 to 231 kDa. As determined using size exclusion chromatography multi-angle light scattering (SEC-MALS), the molecular weight Polydispersity Index was about 2.5.

The content of sodium hyaluronate and nimesulide in the conjugate was assayed using the protocols of Pharmpur method PPCA025 and Pharmpur Method PPCA017 SEC/UV, respectively, and the results indicate that there are at least 800 mg of HA content and at least 15 mg of NIM content per 1 gram of dry NIM-HA conjugate. The degree of substitution (DS) of the conjugate was then determined based on the molar ratio between the disaccharide unit of HA and the H-NIM. The DS was about 2.5% to 5%, meaning that for every 1,000 disaccharide units, there are 25 to 50 H-NIM molecules conjugated thereto.

(4) Synthesis of NIM-HA Disaccharide Conjugate

Disaccharide unit of D-glucuronic acid and N-acetylglucosamine (HA disaccharide) was reacted with 4-aminonimesulide to give NIM-HA disaccharide conjugate having the following structure:

(II)

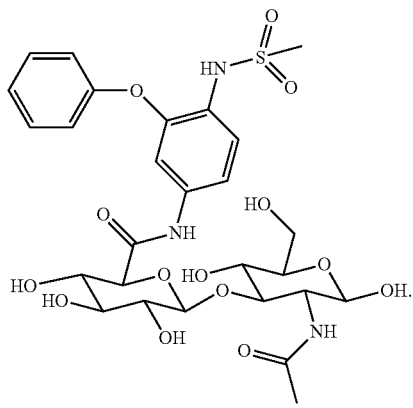

(5) Synthesis of NIM-HA Tetrasaccharide Conjugate

Two disaccharide units of D-glucuronic acid and N-acetylglucosamine (HA tetrasaccharide) was reacted with 4-aminonimesulide to give NIM-HA tetrasaccharide conjugate (NIM-tetra). Briefly, 50 mg of HA tetrasaccharide (HA4) (0.06437 mmol) was dissolved in 3 mL DDW; then, 5 mL DMSO was added to the HA4 solution. 9.1 mg of Oxyma (0.06437 mmol) was dissolved in 0.5 mL DMSO and then added to the HA4 solution under stirring for 6 minutes; then, the 17.9 mg of nimesulide-Boc (0.07081 mmol) was de-protected and then dissolved in 0.5 mL DMSO and added to the HA4 solution. 14 μL DIC (0.09656 mmol) was dissolved in 0.5 mL DMSO under stirring for 1 minute and then added to the HA4 solution. The final reaction mixture was stirred for 48 hours at room temperature, and the resulting solution was freeze dryer for three days and purified by RP-TLC (Merck, 1.05559.0001). The thus-synthesized NIM-tetra has the following structures:

(III)

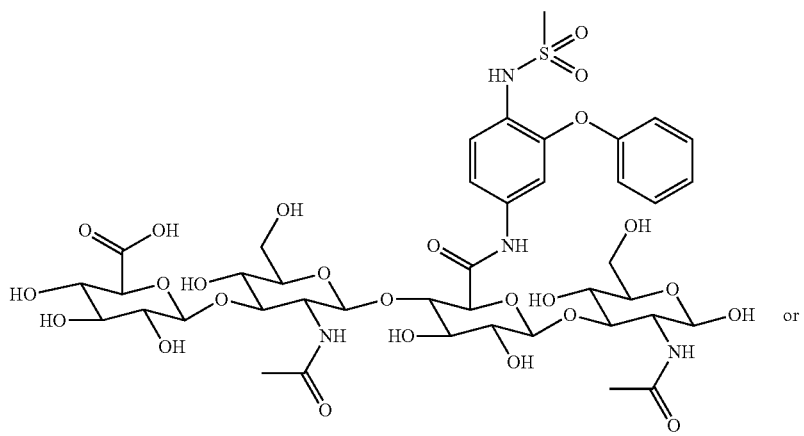 or

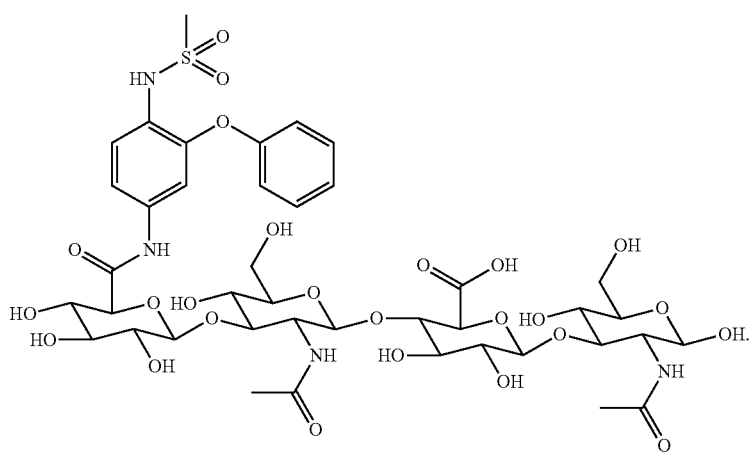

EXAMPLE 2

Effect of NIM-HA Conjugate on PGI2 Expression of Tumor-Bearing Mice

Mice bearing CT26 tumors were created following conventional protocols, and when the tumor volumes reached 25-50 mm$^3$, tumor-bearing mice were randomized to four groups: vehicle control, 50 mg/kg (eq. 1.3 mg/kg Nim) NIM-HA conjugate, 100 mg/kg (eq. 2.6 mg/kg Nim) NIM-HA conjugate, and 200 mg/kg (eq. 5.2 mg/kg Nim) NIM-HA conjugate. The vehicle or test samples were i.v. injected three times weekly for two weeks.

The body weight and tumor volumes were measured three times per week. After two weeks' treatment, mice were sacrificed. Blood was collected by cardiac puncture, and serum was separated and stored at a −80° C. freezer. The tumor tissues were collected either by flash frozen. The serum tissues were utilized for the subsequent correlative analysis.

The prostacyclin (PGI2) level in mice serum was determined following conventional protocols. As summarized in FIG. 1, the results indicate that the administration of 50, 100, or 200 mg/kg (eq. 1.3, 2.6 and 5.2 mg/kg Nim) NIM-HA conjugate can lower the PGI2 level to a statistically significant extent, compared with the vehicle control.

EXAMPLE 3

Effect of NIM-HA Conjugate on IL-6 and IL-6 Downstream Chemokines Expression of Tumor-Bearing mice Mice were handled as described in Example 2 above. When the tumor volumes reached 25-50 mm$^3$, tumor-bearing mice were randomized to six groups: vehicle control, 50 mg/kg NIM-HA (eq. 1.3 mg/kg Nim) conjugate, 100 mg/kg (eq. 2.6 mg/kg Nim) NIM-HA conjugate, 200 mg/kg (eq. 5.2 mg/kg Nim) NIM-HA conjugate, 1.5 mg/kg nimesulide, and 5.3 mg/kg nimesulide. The vehicle or test samples were i.v. injected two times weekly for two weeks.

Figure 2:
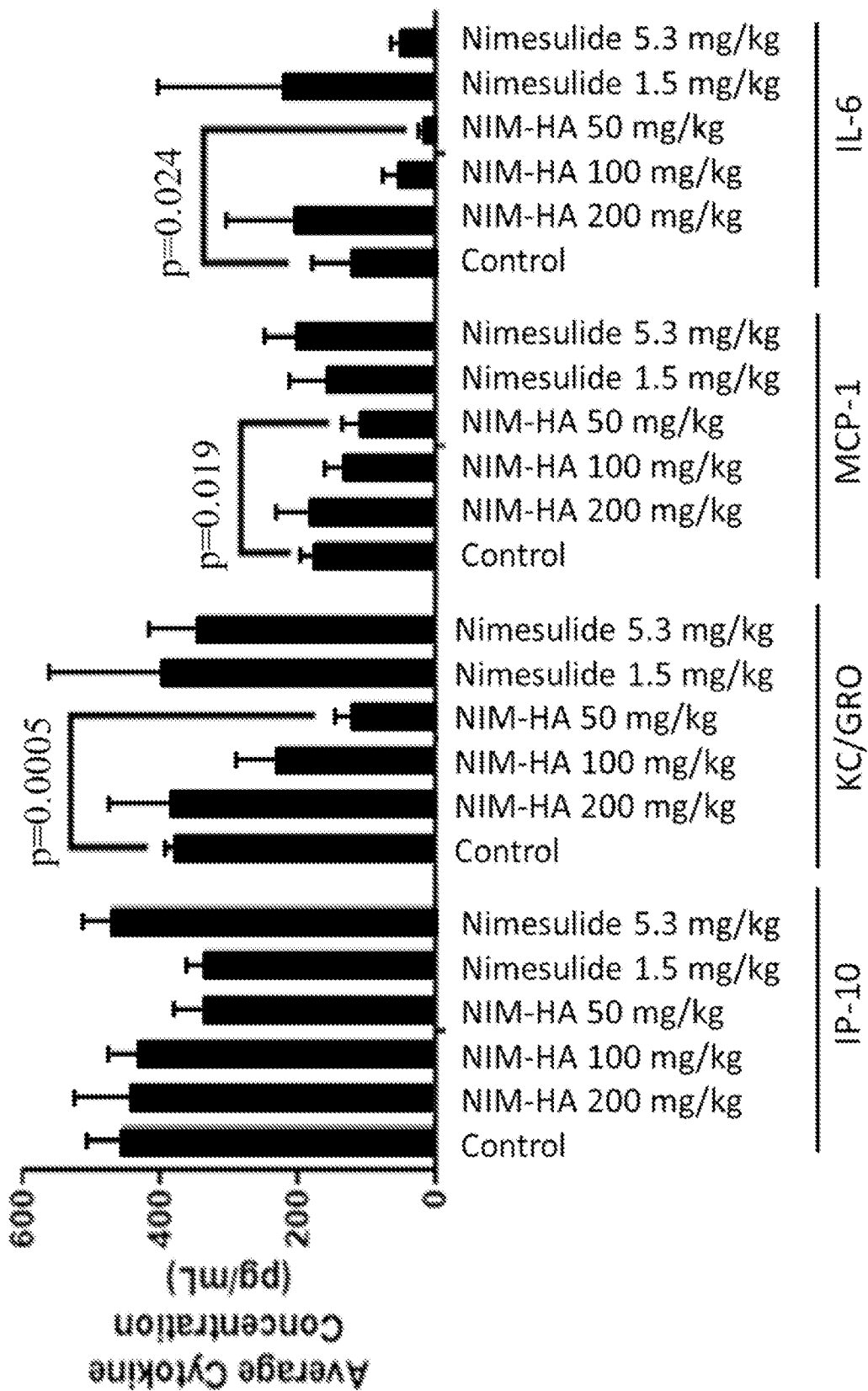
FIG. 2 is a histogram illustrating the average cytokine concentration in mice in different experimental groups according to one working example of the present disclosure.

The serum level of IL-6 and two IL-6 downstream chemokines (KC/GRO and MCP-1) were measured following conventional protocols. As summarized in FIG. 2, the results indicate that the administration of 50 mg/kg (eq. 1.3 mg/kg Nim) NIM-HA conjugate can lower the serum level of IL-6, KC/GRO and MCP-1 to a statistically significant extent, compared with the vehicle control. Also, the administration of 100 mg/kg (eq. 2.6 mg/kg Nim) NIM-HA conjugate can significantly lower the serum level of IL-6 and MCP-1, compared with vehicle control. On the other hand, the administration of a high level of NIM-HA conjugate (200 mg/kg (eq. 5.2 mg/kg Nim)) cannot reduce the serum level of IL-6 and its downstream chemokines. Moreover, a dose-dependency between the dosage of NIM-HA conjugate and the IL-6 blockade effect was found. Further, the administration of nimesulide alone cannot elicit any effect on IL-6 blockade.

EXAMPLE 4

Effect of NIM-HA Conjugates on IL-6 Level in LPS-induced A549 Cells

In this example, A549 cells (human alveolar basal epithelial cells) were used to assess the effect of the present NIM-HA conjugate (CA102N) on the IL-6 level.

A549 cells in 600 μL F-12K medium were seeded in a density of 5×10$^4$ per 24-well and incubated overnight. The next day, the medium was discarded and replaced with a fresh medium containing 1 μg/mL LPS with 0, 0.1, 0.2, 0.4 and 0.8 mg/mL CA102N (eq. 0, 5.9, 11.8, 23.6 and 47.2 μM) conjugate or 5 μg/mL (12.7 μM) dexamethasone, which was then incubated for 48 hours. Then, 300 μL of supernatants were collected, and the IL-6 level was measured using a Human IL-6 Uncoated ELISA kit (Catalogue No. 88-7066; Invitrogen). Cells not treated with LPS are used as the negative control, whereas cells treated with LPS but not CA102N are used as the positive control. The results were summarized in FIG. 3, and the data were expressed as mean±standard deviation (SD).

Figure 3:
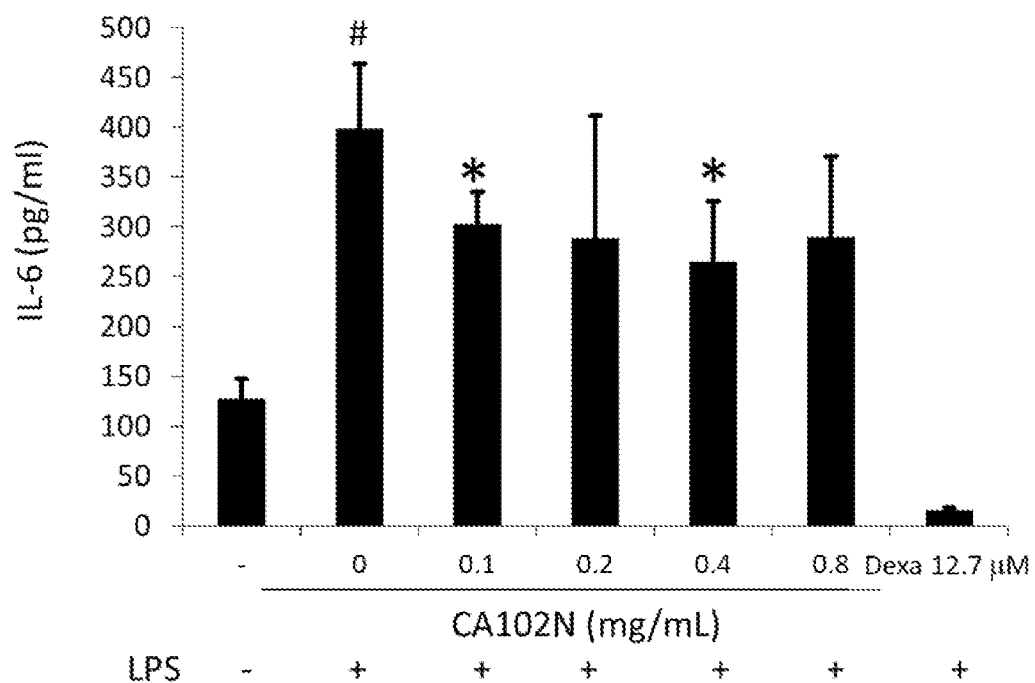
FIG. 3 is a histogram illustrating the effect of NIM-HA on IL-6 level in LPS-induced A549 cells according to one working example of the present disclosure.

The data summarized in FIG. 3 demonstrate that the LPS induction resulted in a significant increase in the IL-6 level, compared with a negative control without LPS induction (#, p<0.05). The treatment with the present NIM-HA conjugate (CA102N) can also substantially decrease the IL-6 level in LPS-treated cells compared with the positive control group where cells were treated with LPS alone (*, p<0.05).

A549 cells in 600 μL F-12K medium were seeded in a density of 2×10$^4$ per 24-well and incubated overnight. The next day, the medium was discarded and replaced with a fresh medium containing 0.5 μg/mL LPS with 0, 4.94, 14.81, 44.4, 133.3 and 400 μM NIM-HA disaccharide conjugate or 10 μM dexamethasone, which was then incubated for 48 hours. Then, 300 μL of supernatants were collected, and the IL-6 level was measured using Human IL-6 Uncoated ELISA kit (Catalogue No. 88-7066; Invitrogen). Cells not treated with LPS are used as the negative control, whereas cells treated with LPS but not NIM-HA disaccharide conjugate are used as the positive control. The results were summarized in FIG. 4, and the data were expressed as mean±standard deviation (SD).

Figure 4:
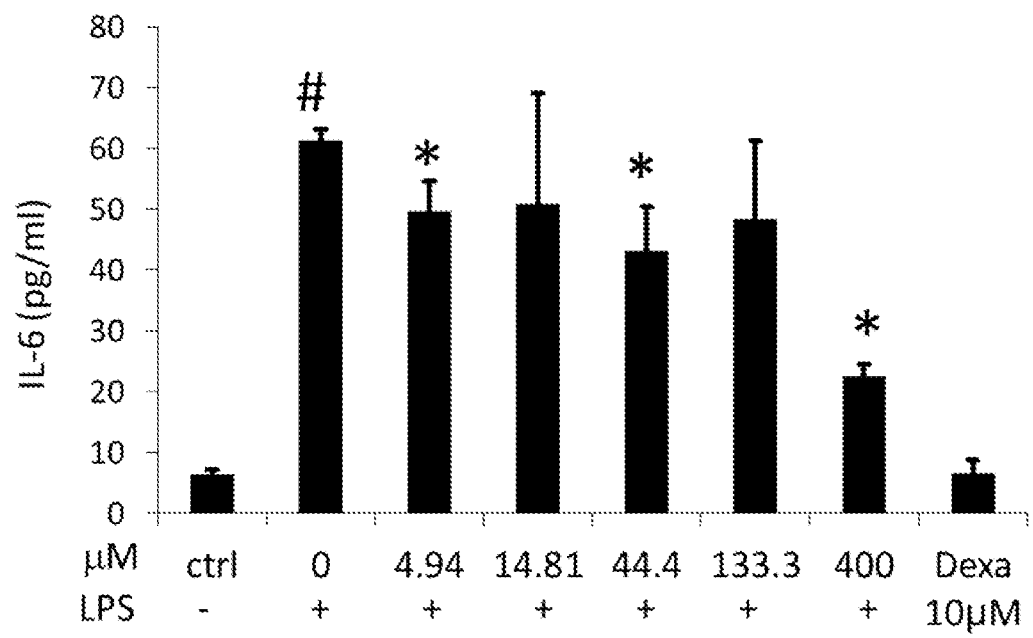
FIG. 4 is a histogram illustrating the effect of NIM-HA disaccharide on IL-6 level in LPS-induced A549 cells according to one working example of the present disclosure.

The data summarized in FIG. 4 demonstrate that the LPS induction resulted in a significant increase in the IL-6 level, compared with a negative control without LPS induction (#, p<0.05). Also, the treatment with the present NIM-HA disaccharide conjugate can substantially decrease the IL-6 level in LPS-treated cells in a dose-dependent manner, compared with the positive control group where cells were treated with LPS alone (*, p<0.05).

EXAMPLE 5

Effect of NIM-HA Conjugate on LPS-Induced Acute Lung Injury Mice

In this example, LPS was used to induce acute lung injury (ALI) in BALB/cByJNarl mice. Various indicators regarding lung injury were examined to investigate the effect of the present hyaluronan conjugate on ALI.

Briefly, male BALB/cByJNarl mice at 5~6-week old were purchased from National Laboratory Animal Center (Taipei, Taiwan) and housed in Chung Shan Medical University (CSMU) Animal Center (Taichung, Taiwan) for 1 week for stabilization. Mice were fasted 12 hours prior to the LPS treatment but allowed water ad libitum. Animals were randomly assigned in to the following 5 groups (n=7 per group): (1) WT group, vehicle control (50 μL water only); (2) LPS group, sham control (50 μL LPS only); (3) LPS+C group, positive control (2 mg/kg methylprednisolone pretreatment/ 50 μL LPS/2 mg/kg methylprednisolone; (4) LPS+L group, low-dose NIM-HA conjugate (CA102N) treatment (50 μL LPS/25 mg/kg CA102N (eq. 0.58 mg/kg nimesulide)); and (5) LPS+M group, medium-dose NIM-HA conjugate (CA102N) treatment (50 μL LPS/50 mg/kg CA102N (eq. 1.16 mg/kg nimesulide)).

For group (1), mice were intratracheally injected with 50 μL water. For group (2), mice were intratracheally injected with 50 μL LPS (1 mg/mL). For group (3), mice were fed with 2 mg/kg methylprednisolone; one hour later, 50 µL LPS (1 mg/mL) was intratracheally injected into mice to induce acute lung injury; and one hour after the LPS injection, mice were given 2 mg/kg methylprednisolone via oral ingestion. For groups (4) and (5), mice were intratracheally injected with 50 µL LPS (1 mg/mL); one hour after the LPS injection, mice of each group were given 25 mg/kg CA102N or 50 mg/kg CA102N via tail vein I.V. injection.

Eighteen hours after the LPS injection, mice were sacrificed by cervical dislocation. The bronchoalveolar lavage fluids (BALFs) were collected using 1.5 ml of PBS flushed fluid from bronchoalveolar, centrifuged at 500×g for 5 minutes at 4° C. to harvest the BALF supernatant. The supernatant was stored at −70° C. for subsequent analysis.

After the sacrifice, the lung was harvested, and the wet weight was measured immediately. The lung was then dried under 65° C. for 48 hours, and the dry weight was measured. The lung wet/dry ratio was calculated for the assessment of the pulmonary edema. For cytokines analysis, ELISA kits (Invitrogen) were used to determine the levels of several cytokines, including TNF-α, IL-1β, and IL-6, in BALFs. The protein concentration was determined using Bradford protein assays.

Figure 5:
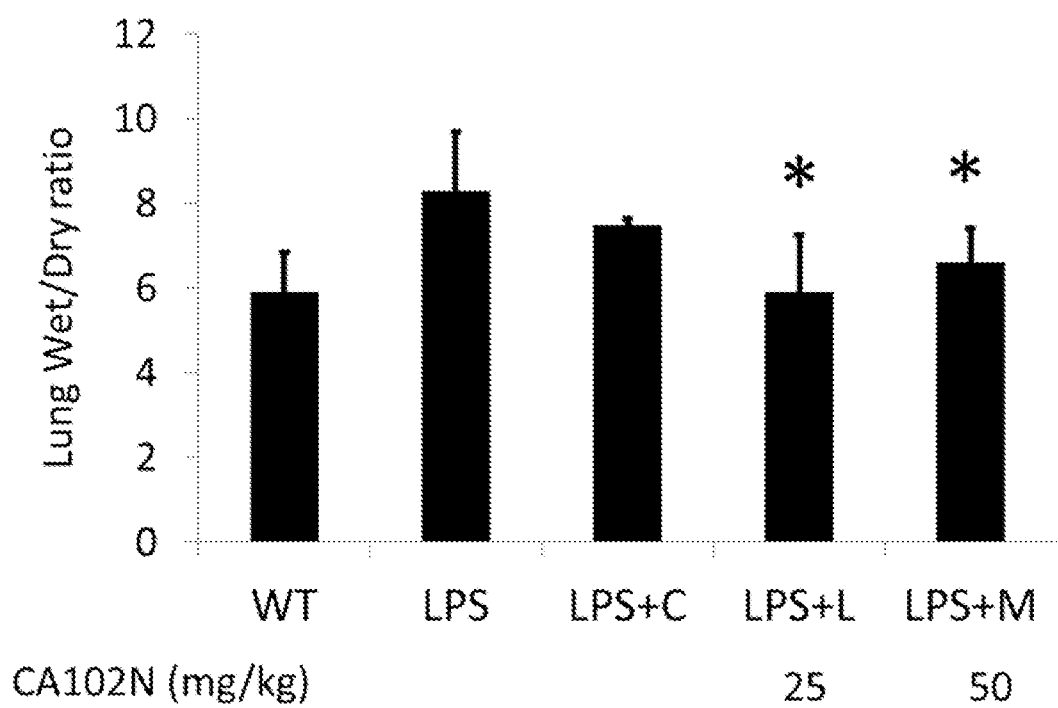
FIG. 5 is a histogram illustrating the effect of NIM-HA on wet/dry ratio of lung weight in LPS-induced ALI mice model according to one working example of the present disclosure.

The data summarized in FIG. 5 indicate that LPS treatment is associated with pulmonary edema. On the other hand, the treatment of methylprednisolone, a corticosteroid medication commonly used to suppress the immune system and decrease inflammation, as well as the low-dose and medium-dose NIM-HA conjugate (CA102N), effectively reduce the extent of pulmonary edema, compared to the LPS group ($p<0.05$), with the latter two groups exhibiting a more profound effect.

Figure 6A:
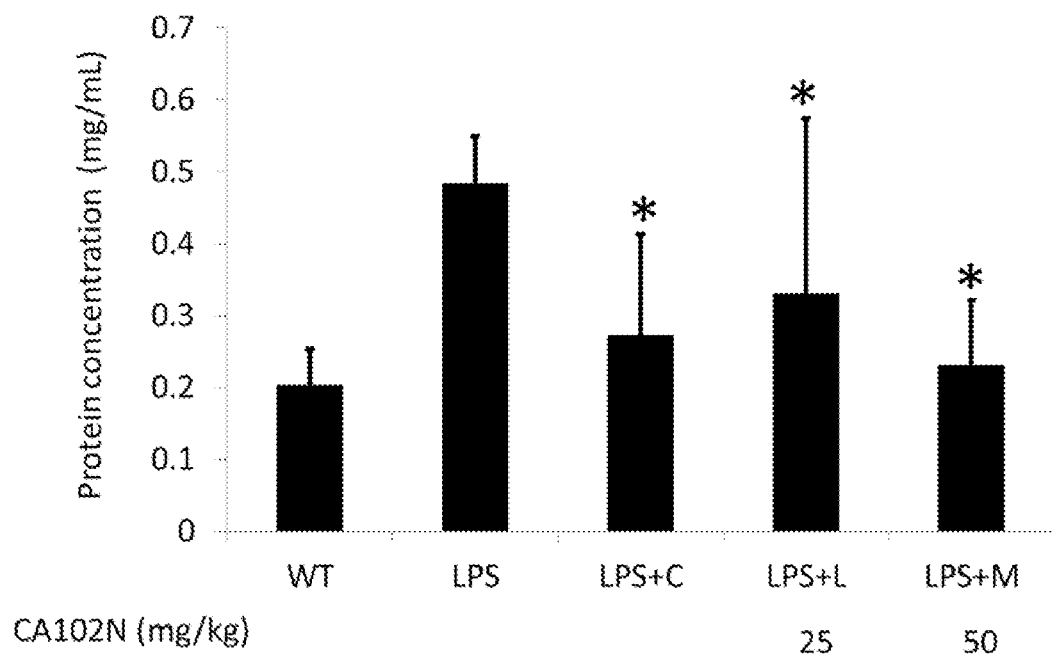
FIG. 6A to 6D are histograms respectively illustrating the effect of NIM-HA on the level of total protein, TNF-α, IL-1β, and IL-6 in BALFs in LPS-induced ALI mice model according to one working example of the present disclosure.
Figure 6B:
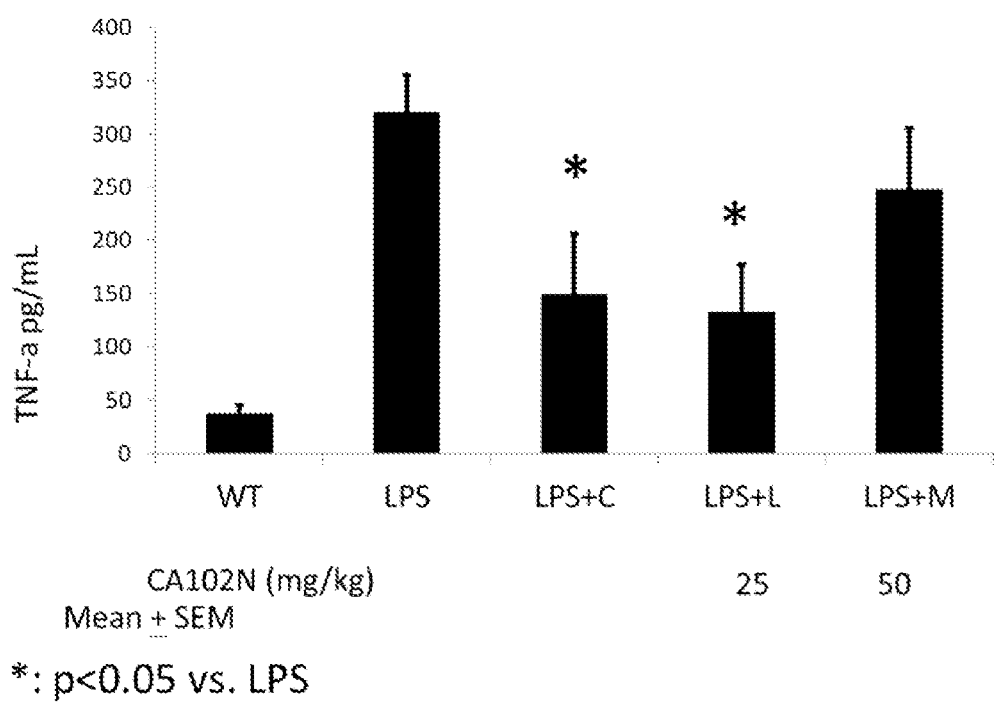
Figure 6C:
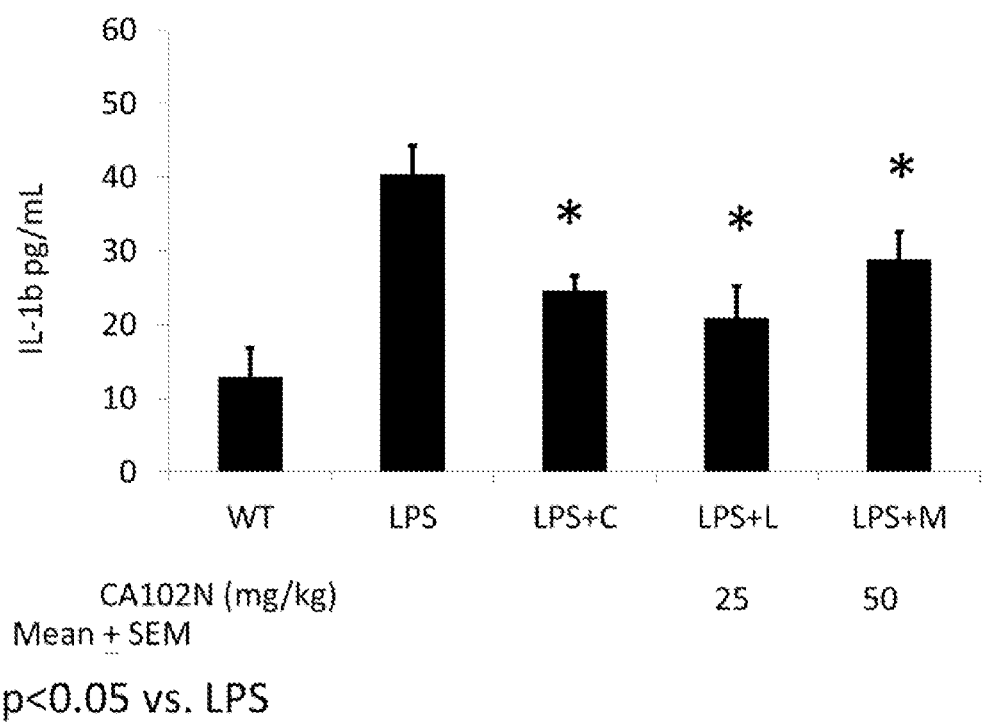
Figure 6D:
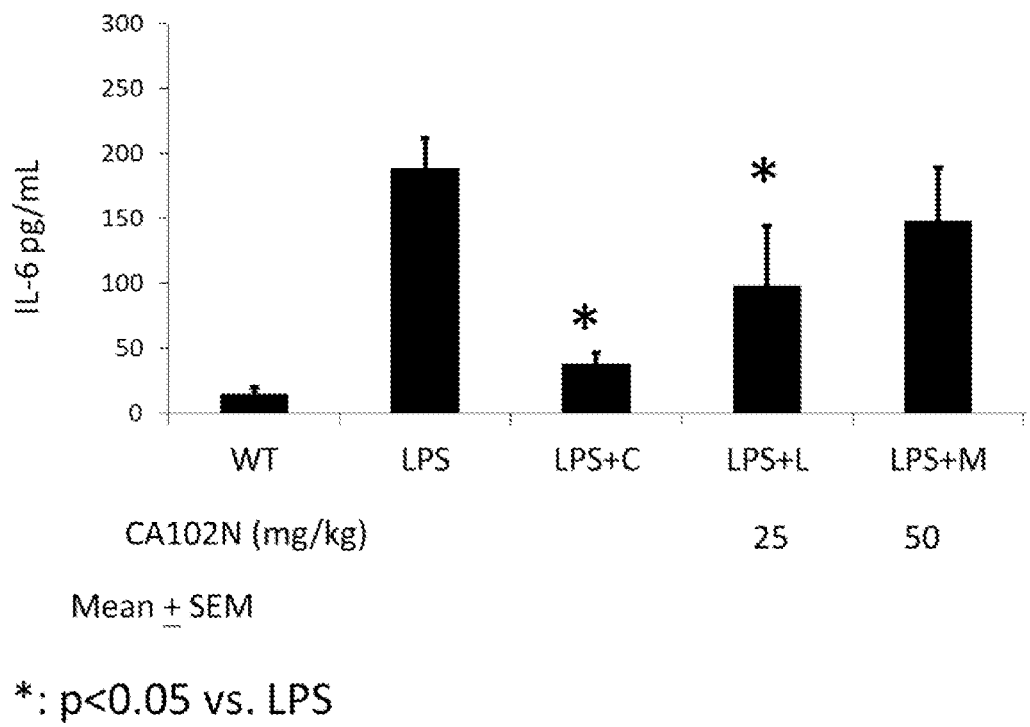

FIG. 6A shows the total protein concentration in BALFs, whereas FIG. 6B to FIG. 6D show the level of TNF-α, IL-1β, and IL-6 in BALFs, respectively. As could be seen in FIG. 6A, in LPS-treated mice, the total protein concentration increases significantly, compared with the WT vehicle control group. The administration of methylprednisolone, low-dose, or medium-dose NIM-HA conjugate (CA102N) reduces the total protein concentration to an extent that is statistically significant compared to the result of the LPS group ($p<0.05$). It should be noted that the total protein concentration of the LPS+M group (mice treated with medium-dose NIM-HA conjugate (CA102N)) is slightly lower than that of the LPC+C group (mice treated with methylprednisolone).

The LPS induction results in an increased level of TNF-α (FIG. 6B), IL-1β (FIG. 6C), and IL-6 (FIG. 6D) in BALFs, whereas the administration of the control drug (methylprednisolone) and low-dose or medium-dose NIM-HA conjugate (CA102N) reduce the expression level of these cytokines in BALFs, compared to the LPS group, with some groups showing the statistical significance ($p<0.05$). It should be noted that the treatment of the low-dose NIM-HA conjugate (CA102N) exhibits a better inhibition to TNF-α and IL-1β expression, compared with the effect of methylprednisolone.

In sum, the results provided in Examples 1 to 5 of the present disclosure show that the present NIM-HA conjugate (CA102N) may effectively block the IL-6 dependent signaling cascade. Moreover, the present disclosure proposed a dosage that is sufficient to elicit such effect.

EXAMPLE 6

Figure 7A:
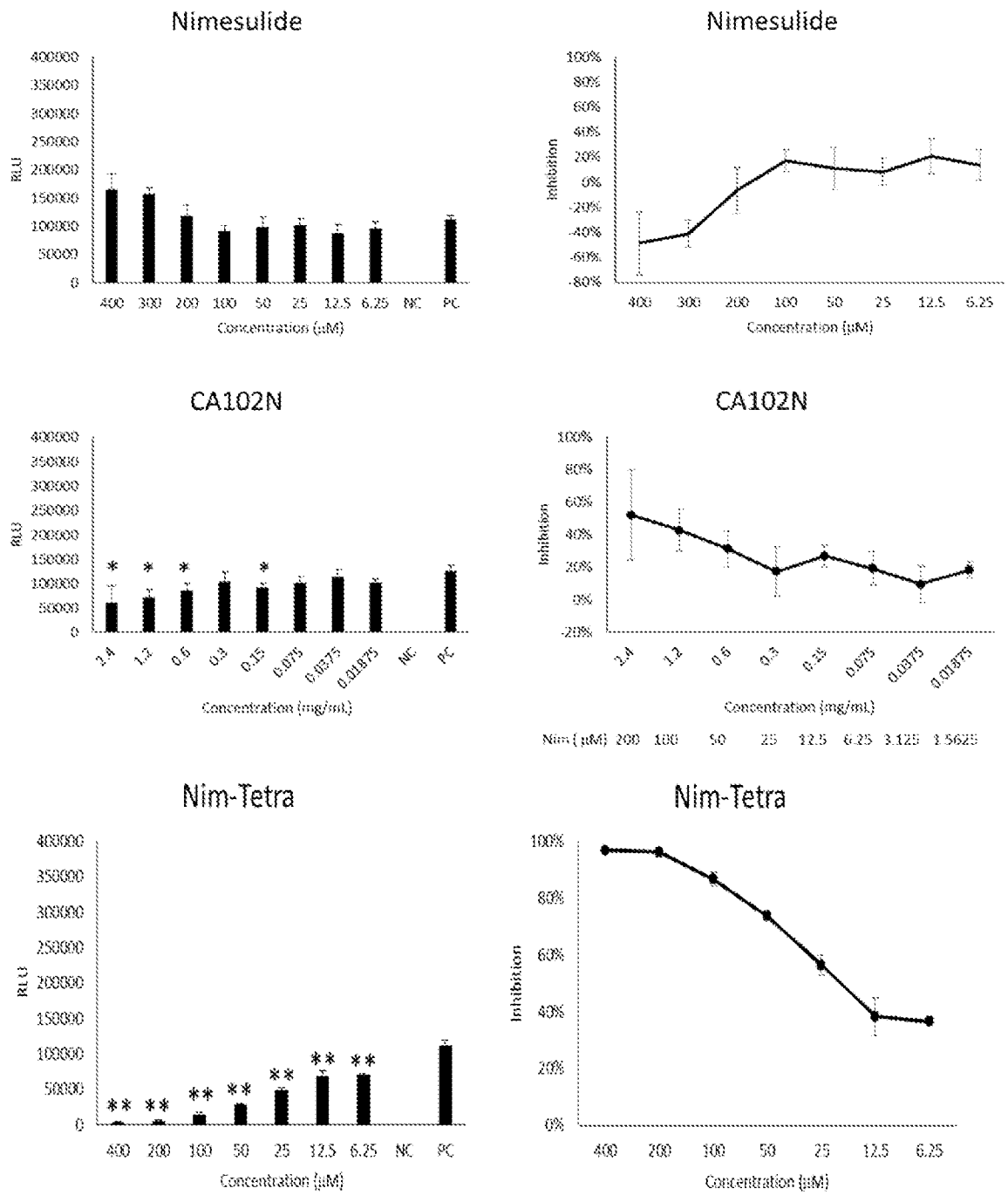
FIG. 7A and FIG. 7B show histograms and line graphs illustrating NIM-HA and NIM-HA4 conjugates' effect on SARS-CoV-2 pseudovirus Entry (blocking entry: 6 hours).
Figure 7B:
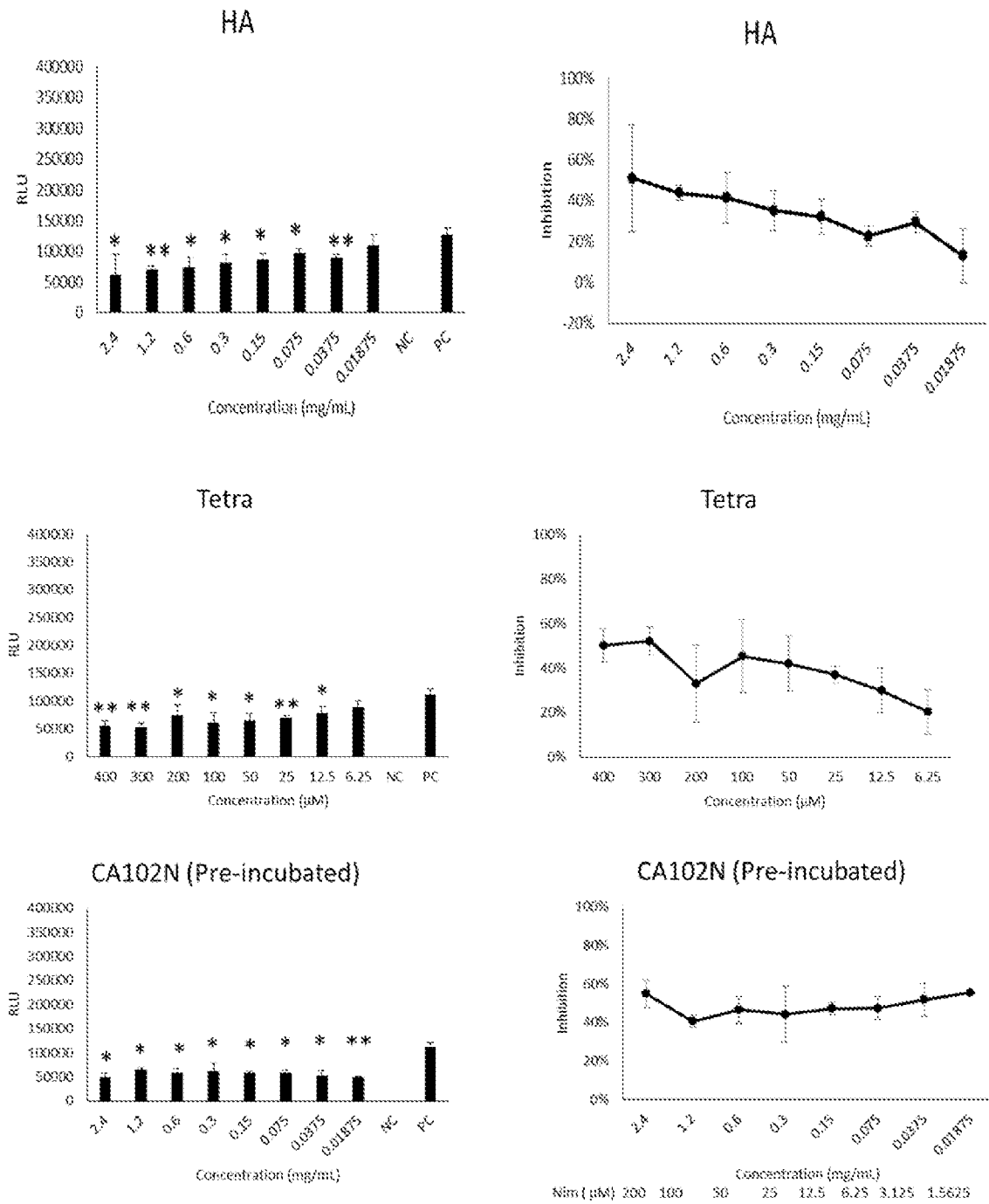

Effect of NIM-HA Conjugate and NIM-Tetra Conjugate on SARS-CoV-2 Pseudovirus Entry HEK-293T cells stably expressing human ACE2 gene were pre-treated with test compounds (nimesulide, NIM-tetra, CA102N, HA, and HA tetrasaccharide (tetra)) of various concentrations in DMEM (supplemented with 10% FBS, 100 U/ml Penicillin/Streptomycin) for 1 hour at 37° C., and followed by co-incubation with 1,000 TU of SARS-CoV-2 pseudotyped lentivirus (SARS-CoV-2 pseudovirus). The culture medium was then replaced with fresh DMEM (supplemented with 10% FBS, 100 U/ml Penicillin/Streptomycin) at 6- or 16-hour post-infection. Besides, in the CA102N (preincubated) group, 1,000 TU of SARS-CoV-2 pseudotyped lentivirus were first pre-treated with CA102N with various concentrations in DMEM for 1 hour at 37° C., and followed by co-incubation with HEK-293T/ACE2 cells for 6 or 16 hours. HEK-293T cells not infected by the pseudotyped lentivirus and not subject to any test compound were used as the negative control (NC), whereas HEK-293T cells infected by the pseudotyped lentivirus but not subject to any test compound were used as the positive control (PC). The cells were continuously cultured for another 48 hours before performing the luciferase assay (Promega Bright-Glo™ Luciferase Assay System), and the percentage of inhibition was calculated as the percentage of the loss of luciferase readout (RLU) in the presence of the test compound to that of no compound control, which can be expressed below: Inhibition %=[(RLU Control−RLU Serum)/RLU Control]*100%. FIGS. 7A and 7B (blocking entry: 6 hours) and FIGS. 8A and 8B (blocking entry: 16 hours) show the results of both the RLU and the percentage of inhibition.

The experimental data summarized in FIGS. 7A and 7B indicate that nimesulide alone cannot inhibit SARS-CoV-2 pseudovirus infection by blocking the viral entry. In contrast, NIM-tetra, CA102N, HA, and HA tetrasaccharide achieve at least 50% inhibition at some tested concentrations in the first 6 hours post-infection. In particular, NIM-tetra exhibits desirable viral inhibition in a dose-dependent manner. Moreover, when the SARS-CoV-2 pseudoviruses were preincubated with CA102N for 6 hours, around 40 to 60% viral entry can be inhibited.

Figure 8A:
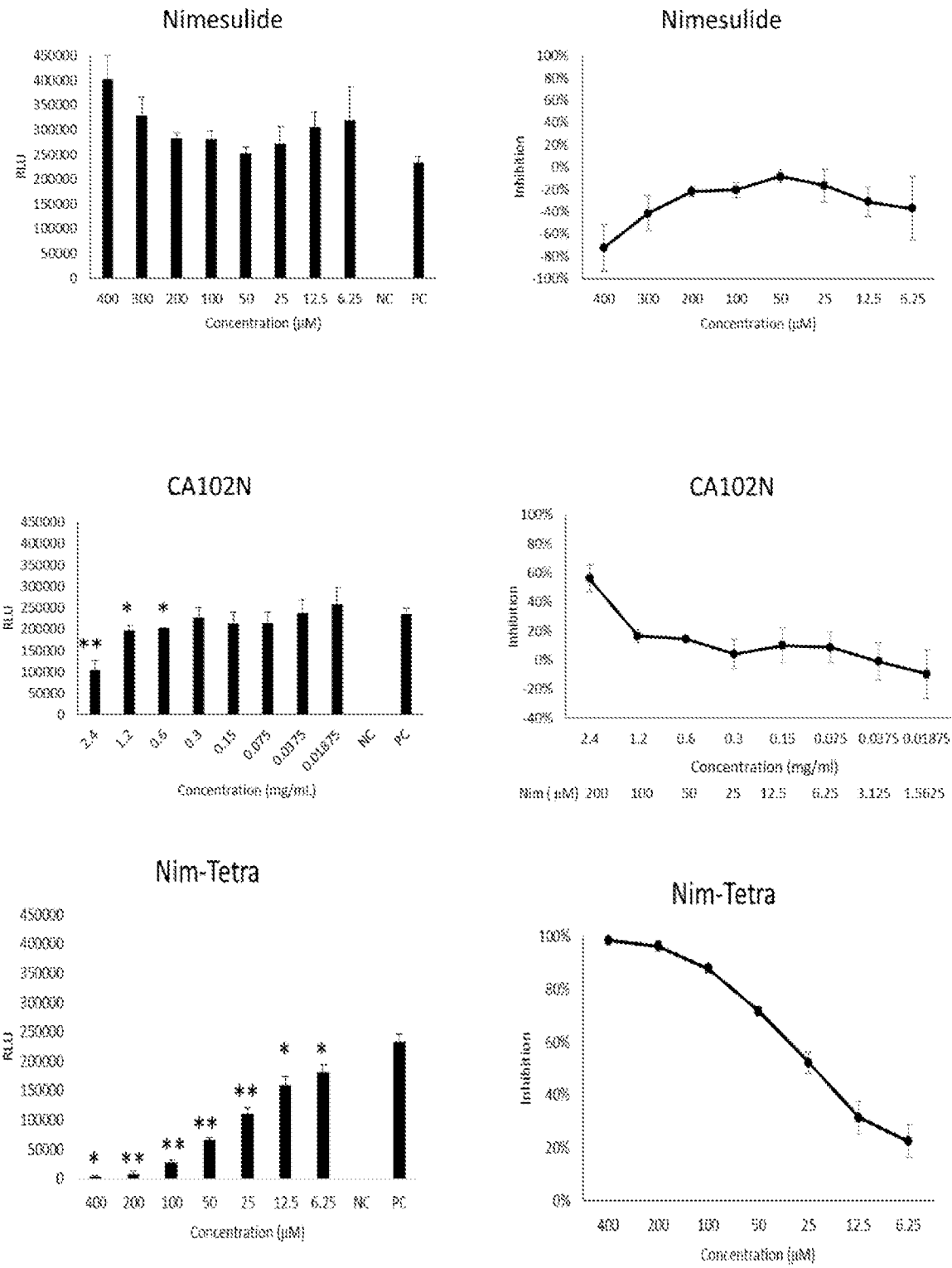
FIG. 8A and FIG. 8B show histograms and line graphs illustrating NIM-HA and NIM-HA4 conjugates' effect on SARS-CoV-2 pseudovirus Entry (blocking entry: 16 hours).
Figure 8B:
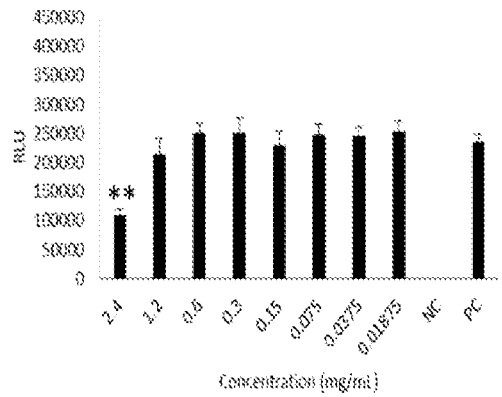
Figure 8B:
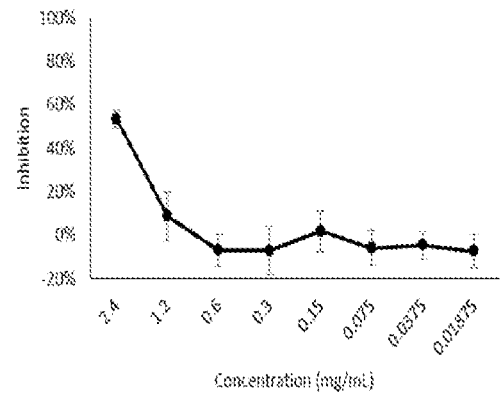
Figure 8B:
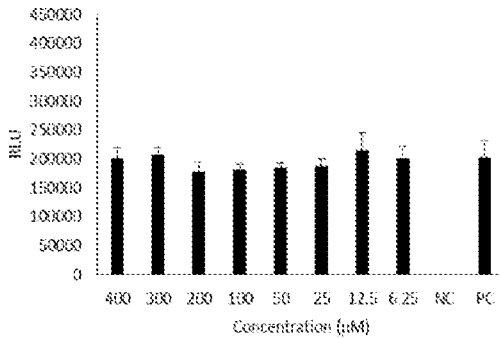
Figure 8B:
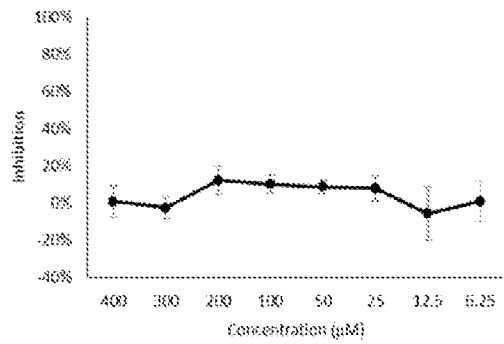
Figure 8B:
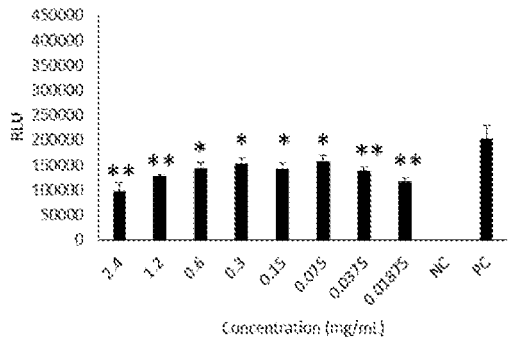
Figure 8B:
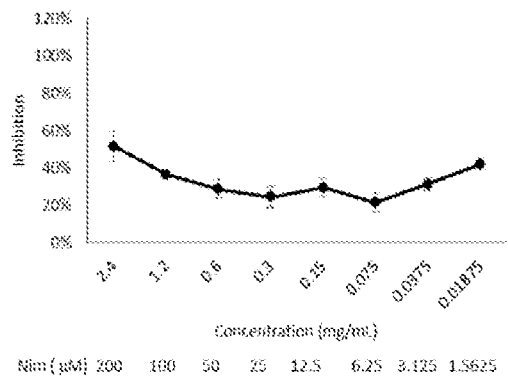

The experimental data summarized in FIGS. 8A and 8B indicate that nimesulide alone cannot inhibit SARS-CoV-2 pseudovirus infection by blocking the viral entry. Besides, HA tetrasaccharide exhibits only marginal inhibition (less than 50% inhibition) at all tested concentrations at the first 16 hours post-infection. Also, both CA102N and HA achieve more than 50% inhibition at the highest test dose. In contrast, NIM-tetra manifests desirable viral inhibition in a dose-dependent manner. Similarly, 50% inhibition is attained when the SARS-CoV-2 pseudoviruses were preincubated with CA102N at the highest test dose for 16 hours.

EXAMPLE 7

Effect of NIM-Tetra Conjugate on Cell Viability

Figure 9A:
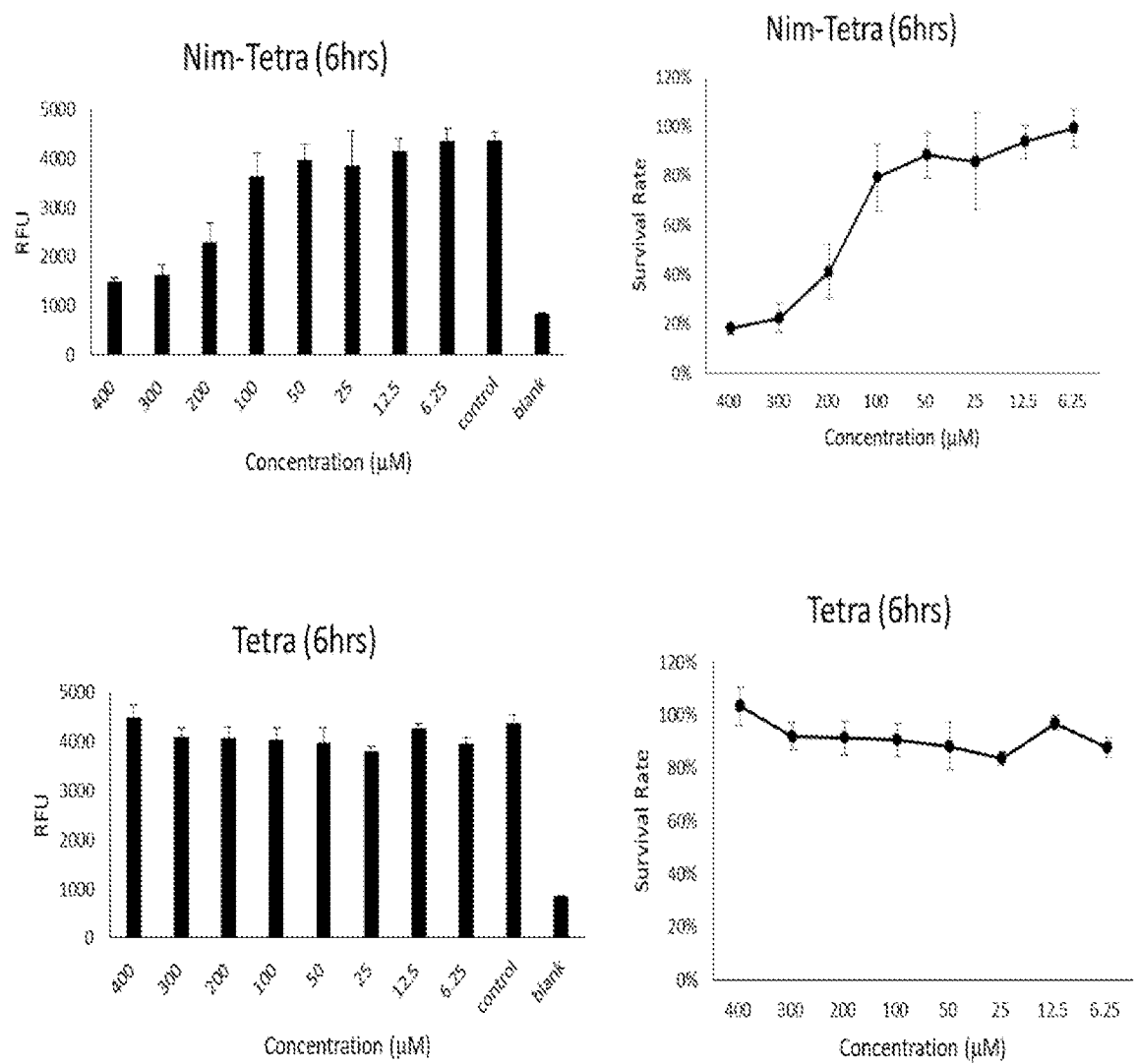
FIG. 9A and FIG. 9B show histograms and line graphs illustrating NIM-HA4 conjugate's effect on the cell viability.
Figure 9B:
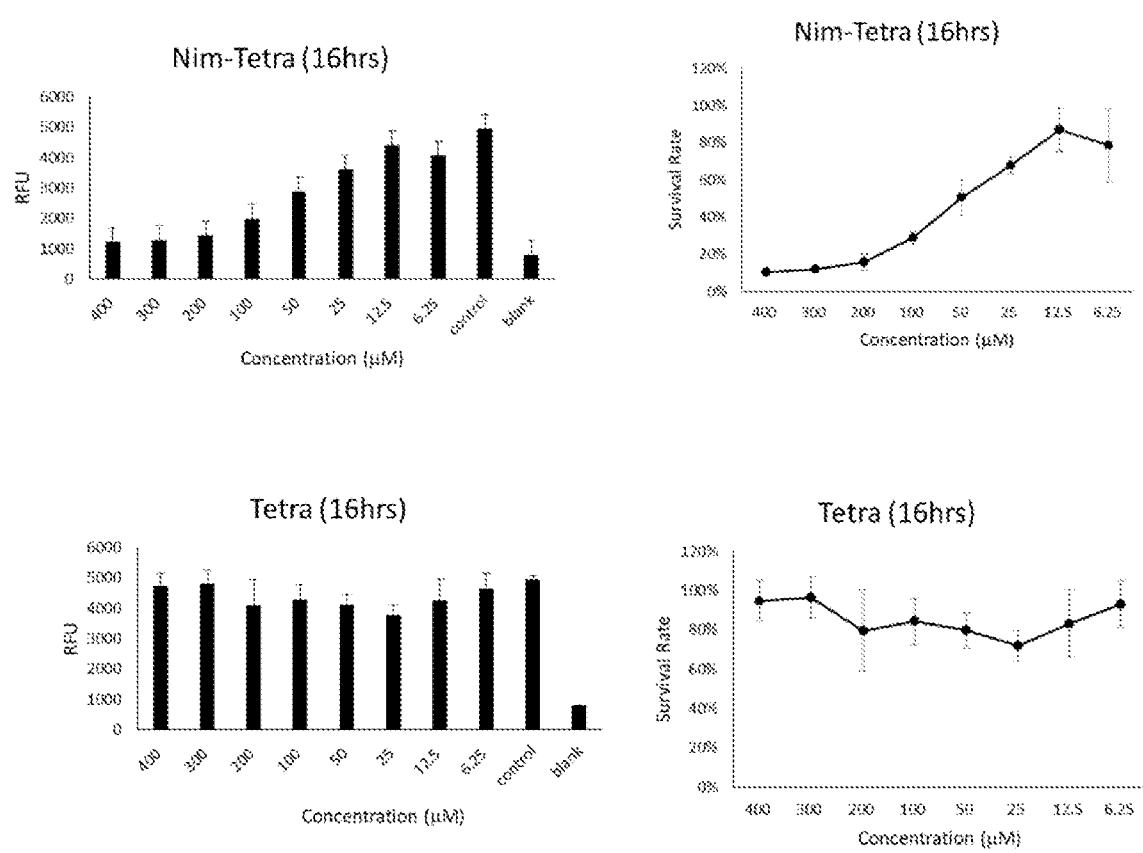

HEK-293T cells stably expressing human ACE2 gene were pre-treated with test compounds (NIM-tetra and HA tetrasaccharide) of various concentrations in DMEM (supplemented with 10% FBS, 100 U/ml Penicillin/Streptomycin) at 37° C. After 6 hours or 16 hours, the culture medium was then replaced with fresh DMEM (supplemented with 10% FBS, 100 U/ml Penicillin/Streptomycin), and cells were continuously cultured for another 48 hours before performing the cell viability assay (Invitrogen™ alamarBlue™ reagent). Then, alamarBlue reagent was added, and the fluorescence of the resorufin was measured with 560 nm excitation and 590 nm emission. The data were normalized to 100% viable cells assuming that the signal obtained from the vehicle-treated wells corresponded to 100% viable cells, and the cell viability can be expressed as Cell Viability %=[(Experimental RFU−Blank RFU)/(Control RFU−Blank RFU)]*100%. FIGS. 9A and 9B show the cell viability after treating with NIM-tetra or HA tetrasaccharide for 6 or 16 hours.

The data in FIGS. 9A and 9B indicate that Nim-tetra shows a trend of inhibition, and the dose-dependent effect is significant at the long-term treatment (16 hours).

EXAMPLE 8

Effect of NIM-HA Conjugate on in vivo SARS-CoV-2 Pseudovirus Infection 8-week-old female BALB/c mice (purchased from BioLASCO Taiwan Co., Ltd.) were allowed to adapt to the laboratory housing for 1 to 2 weeks. After adaption, mice were given 200 µl test samples (CA102N 2:2 mg/kg equivalent of nimesulide; CA102N 4: 4 mg/kg equivalent of nimesulide, or Nimesulide 4:4 mg/kg nimesulide) by intravenous injection for 1 hour and followed by intra-tracheal injection of SARS-CoV-2 pseudovirus ($10^10$ PFU/mouse). 24 hours after the infection, mice were given 100 µl of luciferin via intraperitoneal injection, and the luminescence signal at the lungs was detected and analyzed using IVIS® Spectrum In VIVO Imaging System (PerkinElmer Inc.). The exposure time was 1 minute. Mice not infected by the pseudotyped lentivirus and not subject to any test compound were used as the negative control (the HC group). In contrast, mice infected by the pseudotyped lentivirus but not subject to any test compound were used as the positive control (the Virus group).

Figure 10A:
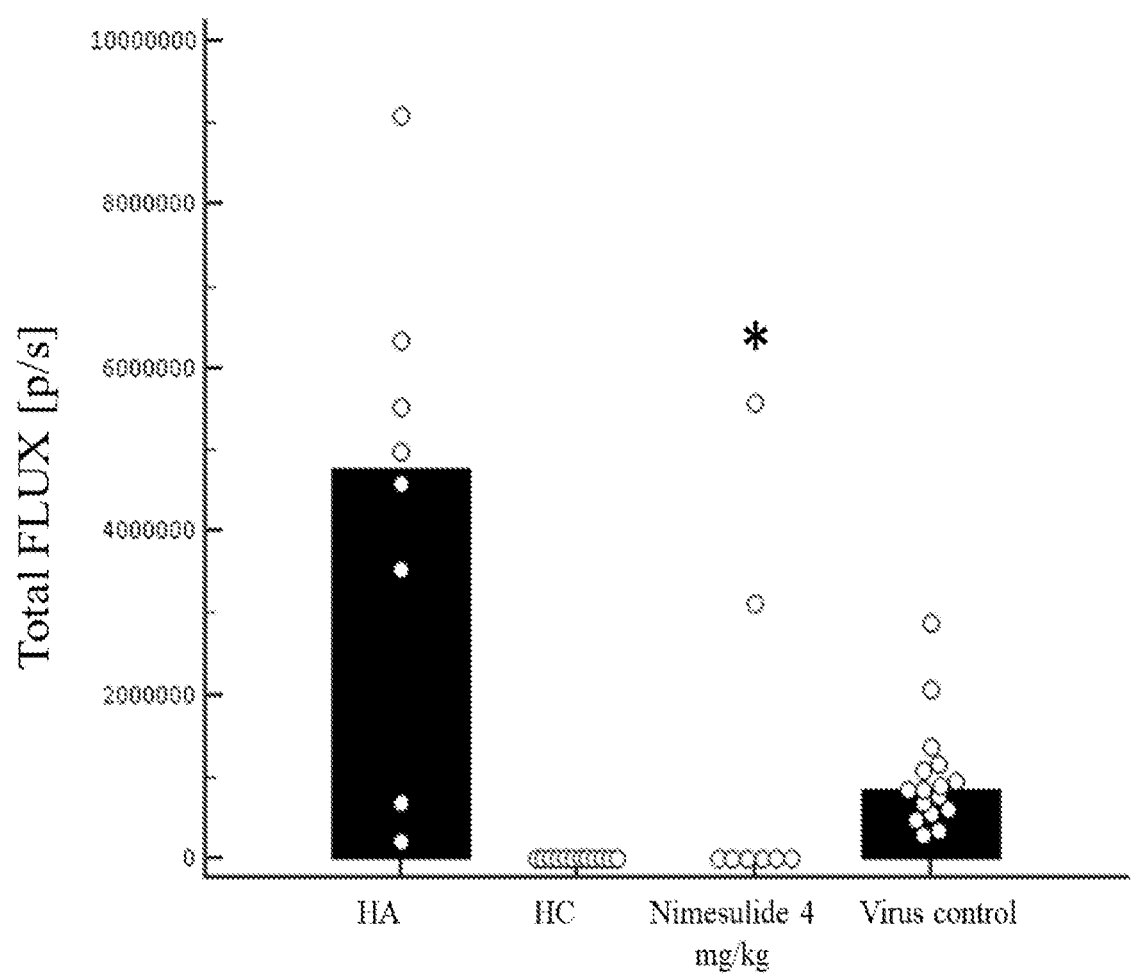
FIG. 10A and FIG. 10B are diagrams of distribution illustrating the in vivo effect of NIM-HA on mice infected by SARS-CoV-2 pseudovirus.
Figure 10B:
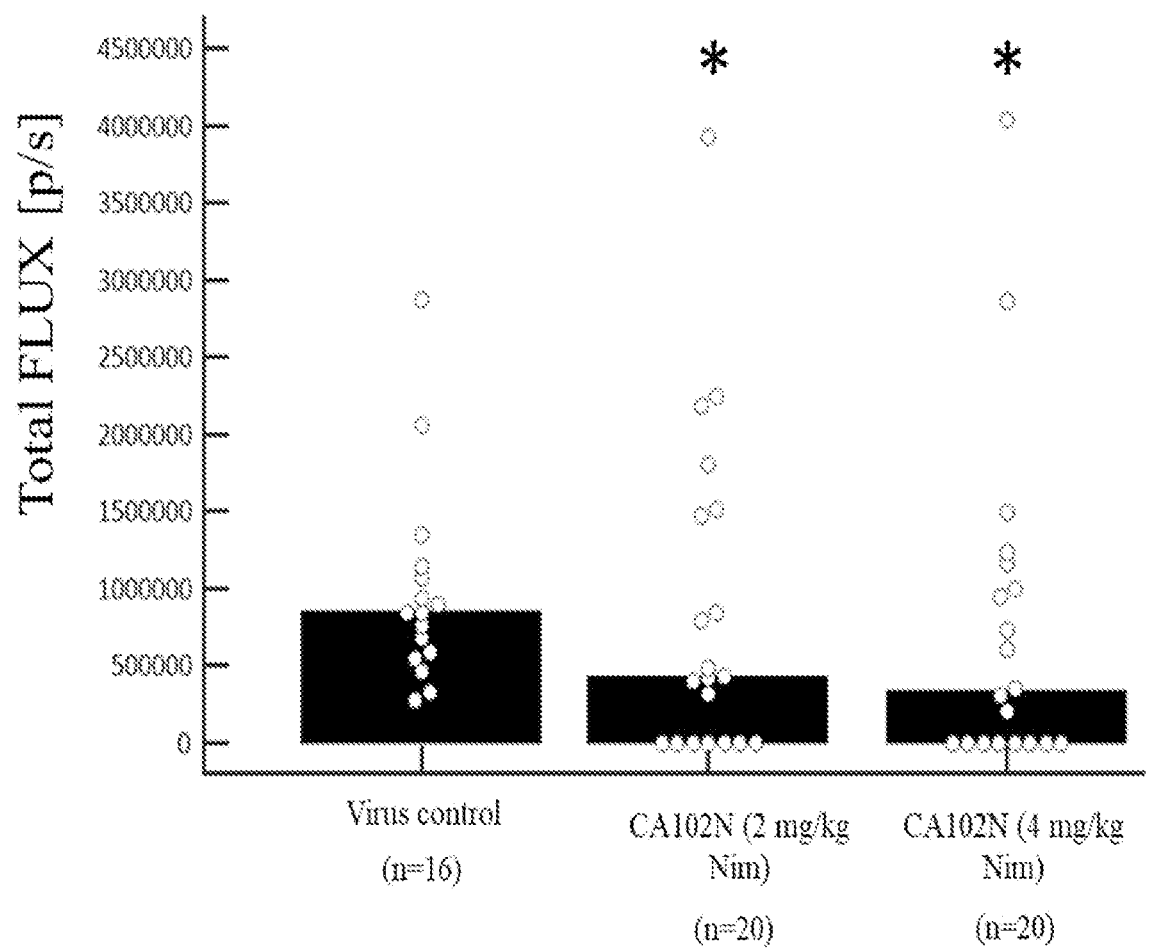

The data summarized in FIGS. 10A and 10B indicate that in nimesulide, CA102N 2, and CA102N 4 groups, SARS-CoV-2 pseudovirus infection is inhibit significantly compared to the positive control (Kruskal—Wallis test and Poisson regression analysis; $p<0.05$). Further analysis shows no statistical difference between either CA102N 2 or CA102N 4 and nimesulide 4. On the other hand, there is no significant difference between the HA group and the positive control.

EXAMPLE 9

Effect of NIM-Tetra Conjugate on SARS-CoV-2 Virus Reduction

Vero B6 cells were seeded in 48-well plates at a density of $10^5$ cells per well. Drugs (3.13 µM and 12.5 µM Nim-tetra and 2.5 µM remdesivir; n=4) were preincubated with 100 µl of SARS CoV-2 virus-containing medium (MOI=0.03) for one hour, and then added into each well after removing the medium on Vero E6 cells. The control group included: (1) background control (no cell), (2) mock infection control for normalization (cells were treated only with medium), and (3) virus control (cells were treated only with viruses). The cells were incubated cells for 1 hour. Thereafter, the medium (along with the drugs and viruses) was removed, and the cells in each well is washed with 37° C. pre-warmed PBS trice. Each well (other than the control) was incubated with 200 µL of drug dilutions for 24 hours, and the supernatant in each well was collected for virus qRT-PCR to determine the virus Ct value. The virus Ct values were expressed as virus copies per ml using known stand curve of Ct vs virus copies.

Figure 11:
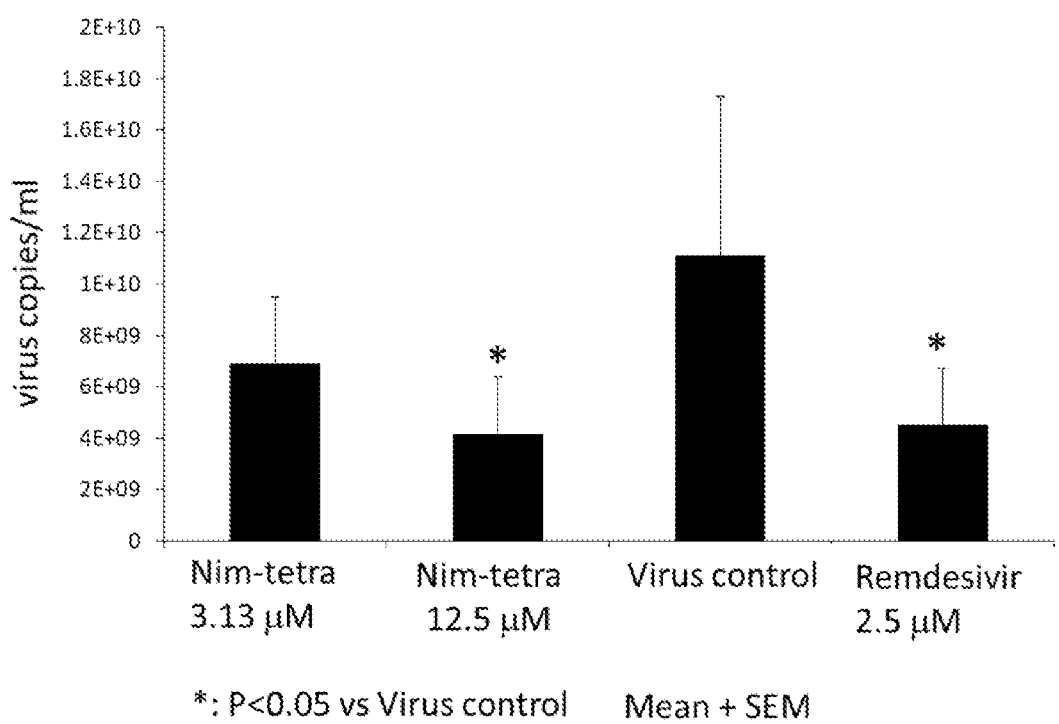
FIG. 11 is a histogram illustrating Nim-tetra (NIM-HA4) conjugate's inhibitory effect to SARS CoV-2 viruses.

The results, as summarized in FIG. 11 indicated that Nim-tetra (Nim-HA4) reduces the virus copy at 3.13 and 12.5 µM and the treatment of 12.5 µM Nim-tetra effectively reduces the virus copy in the Vero E6 cells to a statistically significant level, compared with the virus control group. Also, the treatment of 12.5 µM Nim-tetra shows comparable (and slightly better) inhibitory effect on SARS CoV-2 virus infection as 2.5 µM remdesivir.

In sum, the results provided in Examples 6 to 9 of the present disclosure show that the present NIM-HA conjugate (either CA102N or Nim-tetra) may effectively inhibit the virus infection at least by blocking the viral entry. Moreover, the present disclosure proposed a dosage that is sufficient to elicit such effect.

The present disclosure establishes that the present NIM-HA conjugates may work in dual modalities for treating SARS-CoV-2 virus infection (including coronavirus disease 2019 (COVID-19)) by (1) blocking the IL-6 dependent signaling cascade and (2) blocking the viral entry. Prior studies showed that nimesulide is significantly associated with hepatotoxicity. The experimental data presented herein indicate that the present NIM-HA conjugate can be given at a one-half dose to the dose of nimesulide while achieving a substantially similar in vivo effect. The present NIM-HA conjugate is also advantageous in having a longer serum half-life, further enhancing its therapeutic effect compared to conventional nimesulide.

It will be understood that the above description of embodiments is given by way of example only and that those may make various modifications with ordinary skill in the art. The above specification, examples, and data provide a complete description of the structure and use of exemplary embodiments of the invention. Although various embodiments of the invention have been described above with a certain degree of particularity or with reference to one or more individual embodiments, those with ordinary skill in the art could make numerous alterations to the disclosed embodiments without departing from the spirit or scope of this invention.

What is claimed is:

1. A hyaluronan conjugate or a pharmaceutically acceptable salt thereof, wherein the hyaluronan conjugate has the structure of, (II)

2. A hyaluronan conjugate or a pharmaceutically acceptable salt thereof, wherein the hyaluronan conjugate has the structure of,

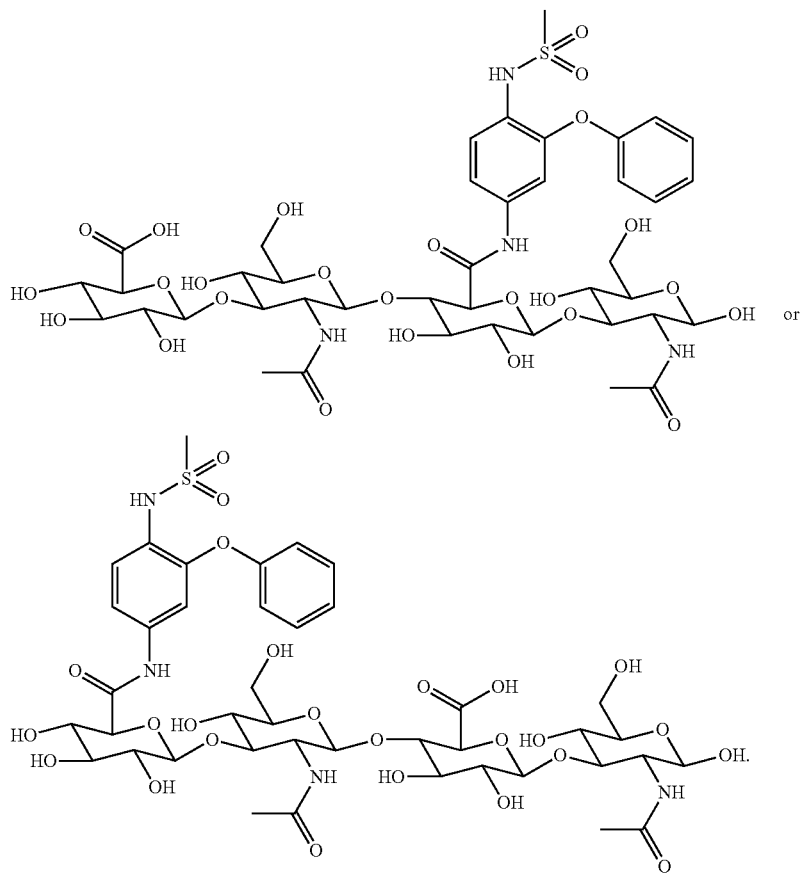

(III)

3. A pharmaceutical composition, comprising an effective amount of a hyaluronan conjugate or a pharmaceutically acceptable salt thereof and a pharmaceutically-acceptable excipient, wherein the hyaluronan conjugate has the structure of,

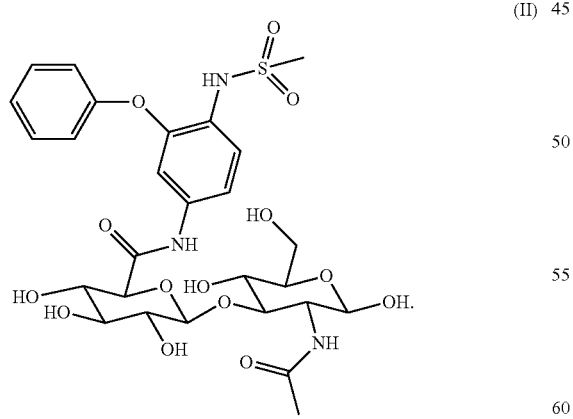

(II)

4. A pharmaceutical composition, comprising an effective amount of a hyaluronan conjugate or a pharmaceutically acceptable salt thereof and a pharmaceutically-acceptable excipient, wherein the hyaluronan conjugate has the structure of,

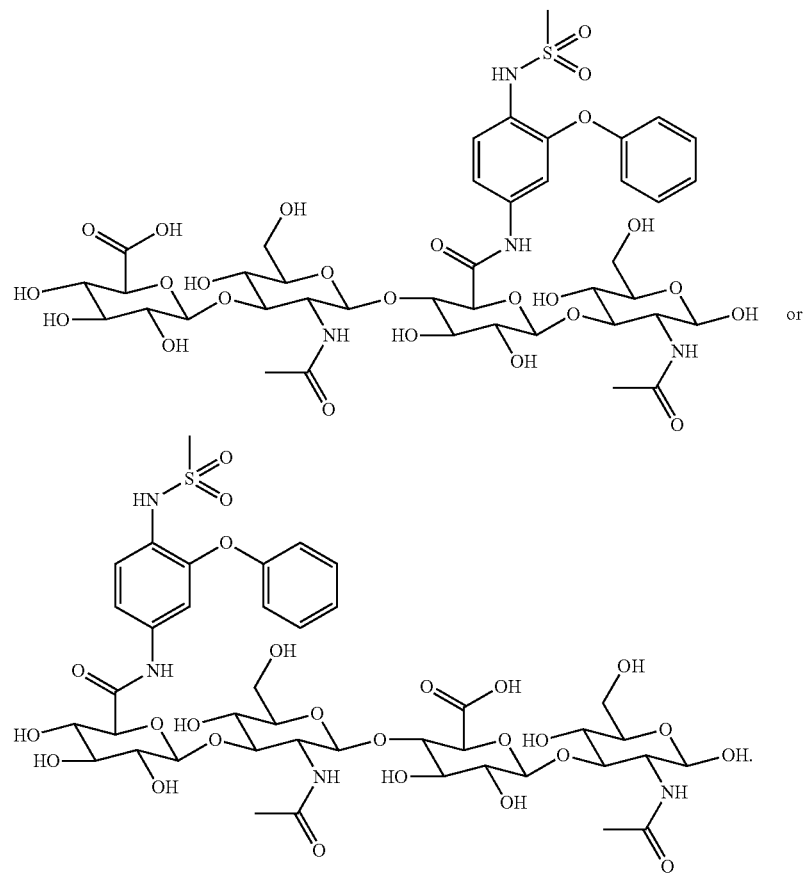
* * * * *